United States Patent [19]
Lee et al.

[11] Patent Number: 6,136,307
[45] Date of Patent: *Oct. 24, 2000

[54] REOVIRUS FOR THE TREATMENT OF CELLULAR PROLIFERATIVE DISORDERS

[75] Inventors: Patrick W. K. Lee; James Strong; Matthew C. Coffey, all of Calgary, Canada

[73] Assignee: Oncolytics Biotech Inc., Calgary, Canada

[*] Notice: This patent is subject to a terminal disclaimer.

[21] Appl. No.: 09/256,824

[22] Filed: Feb. 24, 1999

Related U.S. Application Data

[63] Continuation-in-part of application No. 08/911,383, Aug. 13, 1997.

[51] Int. Cl.$^7$ ..................................................... A61K 39/15
[52] U.S. Cl. ....................................... 424/93.6; 424/215.1
[58] Field of Search ........................... 514/44; 424/215.1, 424/93.6

[56] References Cited

U.S. PATENT DOCUMENTS 4,108,983  8/1978  Wallack .

FOREIGN PATENT DOCUMENTS

| | | |
|---|---|---|
| 0453242A1 | 10/1991 | European Pat. Off. . |
| 0514603 | 11/1992 | European Pat. Off. . |
| 0514603A1 | 11/1992 | European Pat. Off. . |
| 90/09441 | 8/1990 | WIPO . |
| 90/11765 | 10/1990 | WIPO . |
| 94/18992 | 9/1994 | WIPO . |
| 97/04805 | 2/1997 | WIPO . |

OTHER PUBLICATIONS

G. Hashiro et al., "The Preferential Cytotoxicity of Reovirus for certain transformed cell lines", *Archives of Virology* 54(4):307–315 (1977).

J.E. Strong et al., "The Molecular Basis of Viral Oncolysis: Usurption of the Ras signaling Pathway by Reovirus", *The EMBO Journal* 17(12):3351–3362 (Jun. 15, 1998).

Tang et al., "Short communications: Recognitiion of the Epidermal Growth Factor Reeptor by Reovirus" *Virology* 197:412–414 (1993).

Sharp et al., "Homologous regions of the α subunit of eukaryotic translational initiation factor 2 (eIF2α) and the vaccinia virus K3L gene produt interact with the same domain within the dsRNA–activated protein kinase (PKR)" *Eur. J. Biochem.* 250:85–91 (1997).

Randazzo et al., "Herpes Simplex virus 1716, and ICP 34.5 null mutant, is unable to replicate in CV–1 cells due to a translational block that can be overcome by coinfection with SV40" *J. of Gen. Virol.* 78:3333–3339 (1997).

He et al., "Suppression of the phenotype of γ1 34.5– herpes simplex 1: Failure of activated RNA–dependent protein kinase to shut off protein synthesis is associated with a deletion in the domain of the α47 Gene" *J. of Virol.* 71(8):6049–6054 (Aug. 1997).

Gale, Jr. et al., "Evidence that hepatitis C virus resistance to interferon is mediated through repression of the PKR protein kinase by the nonstructural 5A protein" *Virology* 230:217–227 (1997).

Kawagishi–Kobayashi et al., "Regulation of the protein kinase PKR by the vaccinia viurs pseudosubstrate inhibitor K3L is dependent on residues conserved between the K3L protein and the pKR substrate 3IF2α" *Mol. and Cell Biol.* 17(7):4146–4158 (1997).

Cahill, M. A., et al., "Signalling pathways: Jack of all cascades," Current Biology, 6(1): 16–19 (1996).

Macara, I. G., et al., "The Ras superfamily og GTPases," The FASEB Journal, 10: 625–630 (1996).

Marshall, C. J., "Ras effectors," Current Opinion in Cell Biology, 8:197–204 (1996).

Strong, J. E. et al., "Evidence That the Epidermal Growth Factor Receptor on Host Cells Confers Reovirus Infection Efficiency," Virol. 197:405–411 (1993).

Duncan, M. R., et al., "Differential Sensivivity of Normal and Transformed Human Cells to Reovirus Infection," J. of Virol. 28 (2):444–449 (1978).

Soroceanu, L. et al., "Use of Genetically Engineered HSV–1 Viruses in Treatment of Malignant Intracerebral Gliomas," FASEB.J. 9(3): Abstract 812 p. A139 (1995).

Andreansky, S.S. et al., "The application of genetically engineered herpes simplex viruses to the treatment of experimental brain tumors," Proc. Natl. Acad. Sci. USA 93:11313–11318 (1996).

Boviatsis, E.J., et al., "Antitumor activity and reporter gene transfer into rat brain neoplasms inoculated with herpes simplex virus vectors defective in thymidine kinase or ribonucleotide reductase," Gene Therapy 1:323–331 (1994).

Taterka, J. et al., "Characterization of Cytotoxic Cells from Reovirus–Infected SCID Mice: Activated Cells Express Natural Killer–and Lymphokine–Activated Killer–Like Activity but Fall to Clear Infection," J. of Virol. 69 (6): 3910–3914 (1995).

(List continued on next page.)

*Primary Examiner*—Terry McKelvey
*Attorney, Agent, or Firm*—Burns, Doane, Swecker & Mathis, LLP

[57] ABSTRACT

Methods for treating proliferative disorders, by administering reovirus to a Ras-mediated proliferative disorder, are disclosed. The reovirus is administered so that it ultimately directly contacts ras-mediated proliferating cells. Proliferative disorders include but are not limited to neoplasms. Human reovirus, non-human mammalian reovirus, and/or avian reovirus can be used. If the reovirus is human reovirus, serotype 1 (e.g., strain Lang), serotype 2 (e.g., strain Jones), serotype 3 (e.g., strain Dearing or strain Abney), as well as other serotypes or strains of reovirus can be used. Combinations of more than one type and/or strain of reovirus can be used, as can reovirus from different species of animal. Either solid neoplasms or hematopoietic neoplasms can be treated.

36 Claims, 6 Drawing Sheets

OTHER PUBLICATIONS

Zhang, J.F., et al., "Treatment of a human breast cancer xenograft with an adenovirus vector containing an interferon gene results in rapid regression due to viral oncolysis and gene therapy," Proc. natl. Acad. Sci. USA 93:4513–4518 (1996).

Chambers, R. et al., "Comparison of genetically engineered herpes simplex viruses for the treatment of brain tumors in a scid mouse model of human malignant glioma," Proc. Natl. Acad. Sci. USA 92:1411–1415 (1995).

Williams, M.E. et al., "Rejectin of reovirus–treated L1210 leukemia cells by mice," Cancer Immunol. Immunother. 23:87–92 (1986).

Theiss, J.C. et al., "Effect of Reovirus Infection on Pulmonary Tumor Response to Urethan in Strain A Mice," J. Natl. Cancer Inst 61:131–134 (1978).

Kollermorgen, G.M. et al., "Immunotherapy of EL4 Lymphoma with Reovirus," Cancer Immunol. Immunother. 1:239–244 (1976).

Bryson, J.S. and Cox, D.C., "Characteristics of reovirus–mediated chemoimmunotherapy of murine L1210 leukemia," Cancer Immunol. Immunother. 26: 132–138 (1988).

Gentsch, J.R. and Pacitti, A.F., Effect of Neuraminidase Treatment of Cells and Effect of Soluble Glycoproteins on Type 3.

Strong, J.E. et al., "Evidence That the Epidermal Growth Factor Receptor on Host Cells confers Reovirus Infection Efficiency," Virology 197:405–411 (1993).

Hershey, J.W.B., "Translation Cntrol in Mammalian Cells," Annu. Rev. Biochem. 60:717–755 (1991).

Steele et al, Cancer Biotherapy, vol. 10 (4): pp. 307–315, 1995.

Strong et al, Journal of Virology, vol. 70 (1): pp. 612–616, Jan, 1996.

Barbacid, Annu7al Review of Biochemistry, vol. 56: pp. 779–827, 1987.

Effect of Reovirus on Mouse Tumors Grown in Mice with an Immune System

Effect of Reovirus on Mouse Tumors Grown in Mice with an Immune System

REOVIRUS FOR THE TREATMENT OF CELLULAR PROLIFERATIVE DISORDERS

CROSS REFERENCE TO RELATED APPLICATION

This application is a continuation-in-part application of U.S. application Ser. No. 08/911,383 filed Aug. 13, 1997 which is incorporated herein by reference in its entirety.

BACKGROUND OF THE INVENTION

1. Field of the Invention

The present invention pertains to methods for treating ras-mediated proliferative disorders in a mammal using reovirus.

2. References

The following publications, patent applications and patents are cited in this application:

U.S. Pat. No. 5,023,252

Armstrong, G. D. et al. (1984), *Virology* 138:37;

Aronheim, A., et al.,(1994) *Cell*, 78:949–961

Barbacid, M., *Annu. Rev. Biochem.*, 56:779–827 (1987);

Berrozpe, G., et al. (1994), *Int. J. Cancer,* 58:185–191

Bischoff, J. R. and Samuel, C. E., (1989) *Virology,* 172:106–115

Cahill, M. A., et al., *Curr. Biol.,* 6:16–19 (1996);

Chandron and Nibert, "Protease cleavage of reovirus capsid protein mu1 and mu1C is blocked by alkyl sulfate detergents, yielding a new type of infectious subvirion particle", *J. of Virology* 72(1):467–75 (1998)

Chaubert, P. et al. (1994), *Am. J. Path.* 144:767; Bos, J. (1989) *Cancer Res.* 49:4682

Cuff et al., "Enteric reovirus infection as a probe to study immunotoxicity of the gastrointestinal tract" *Toxicological Sciences* 42(2):99–108 (1998)

Der, S. D. et al., *Proc. Natl. Acad. Sci. USA* 94:3279–3283 (1997)

Dudley, D. T. et al., *Proc. Natl. Acad. Sci. USA* 92:7686–7689 (1995)

Duncan et al., "Conformational and functional analysis of the C-terminal globular head of the reovirus cell attachment protein" *Virology* 182(2):810–9 (1991)

Fields, B. N. et al. (1996), *Fundamental Virology,* 3rd Edition, Lippincott-Raven;

Gentsch, J. R. K. and Pacitti, A. F. (1985), *J. Virol.* 56:356;

E. Harlow and D. Lane, "Antibodies: A laboratory manual", Cold Spring Harbor Laboratory (1988)

Helbing, C. C. et al., *Cancer Res.* 57:1255–1258 (1997)

Hu, Y. and Conway, T. W. (1993), *J. Interferon Res.,* 13:323–328

Laemmli, U. K., (1970) *Nature,* 227:680–685

Lee. J. M. et al. (1993) *PNAS* 90:5742–5746;

Lee, P. W. K. et al. (1981) *Virology,* 108:134–146

Levitzki, A. (1994) *Eur. J. Biochem.* 226:1; Janes, P. W., et al. (1994) *Oncogene* 9:3601; Bos, J. (1989) *Cancer Res.* 49:4682

Lowe. S. W. et al. (1994) *Science,* 266:807–810;

Lyon, H., *Cell Biology, A Laboratory Handbook,* J. E. Celis, ed., Academic Press, 1994, p. 232

Mah et al., "The N-terminal quarter of reovirus cell attachment protein sigma 1 possesses intrinsic virion-anchoring function" *Virology* 179(1):95–103 (1990)

McRae, M. A. and Joklik, W. K., (1978) *Virology,* 89:578–593

Millis, N. E. et al. (1995) *Cancer Res.* 55:1444;

Mundschau, L. J. and Faller, D. V., (1992) *J. Biol. Chem.,* 267:23092–23098

Nagata, L., et al. ,(1984) *Nucleic Acids Res.,* 12:8699–8710

Paul R. W. et al. (1989) *Virology* 172:382–385

Raybaud-Diogene. H. et al. (1997) *J. Clin. Oncology,* 15(3):1030–1038;

*Remington's Pharmaceutical Sciences,* Mace Publishing Company, Philadelphia Pa. $17^{th}$ ed. (1985)

Robinson, M. J. and Cobb, M. H., *Curr. Opin. Cell. Biol.* 9:180–186 (1997);

Rosen, L. (1960) *Am. J. Hyg.* 71:242;

Sabin, A. B. (1959), *Science* 130:966

Samuel, C. E. and Brody, M., (1990) *Virology,* 176:106–113;

Smith, R. E. et al., (1969) *Virology,* 39:791–800

Stanley, N. F. (1967) *Br. Med. Bull.* 23:150

Strong, J. E. et al.,(1993) *Virology,* 197:405411;

Strong, J. E. and Lee, P. W. K., (1996) *J. Virol.,* 70:612–616

Trimble, W. S. et al. (1986) *Nature,* 321:782–784

Turner and Duncan, "Site directed mutagenesis of the C-terminal portion of reovirus protein signal:evidence for a conformation-dependent receptor binding domain" *Virology* 186(1):219–27 (1992);

Waters, S. D. et al., *J. Biol. Chem.* 270:20883–20886 (1995)

Wiessmuller, L. and Wittinghofer, F. (1994), *Cellular Signaling* 6(3):247–267;

Wong, H., et al., (1994) *Anal. Biochem.,* 223:251–258

Yang, Y. L. et al. *EMBO J* 14:6095–6106 (1995)

Yu, D. et al. (1996) *Oncogene* 13:1359

All of the above publications, patent applications and patents are herein incorporated by reference in their entirety to the same extent as if each individual publication, patent application or patent was specifically and individually indicated to be incorporated by reference in its entirety.

3. State of the Art

Normal cell proliferation is regulated by a balance between growth-promoting proto-oncogenes and growth-constraining tumor-suppressor genes. Tumorigenesis can be caused by genetic alterations to the genome that result in the mutation of those cellular elements that govern the interpretation of cellular signals, such as potentiation of proto-oncogene activity or inactivation of tumor suppression. It is believed that the interpretation of these signals ultimately influences the growth and differentiation of a cell, and that misinterpretation of these signals can result in neoplastic growth (neoplasia).

Genetic alteration of the proto-oncogene Ras is believed to contribute to approximately 30% of all human tumors (Wiessmuller, L. and Wittinghofer, F. (1994), *Cellular Signaling* 6(3):247–267; Barbacid, M. (1987) *A Rev. Biochem.* 56, 779–827). The role that Ras plays in the pathogenesis of human tumors is specific to the type of tumor. Activating mutations in Ras itself are found in most types of human malignancies, and are highly represented in pancreatic cancer (80%), sporadic colorectal carcinomas (40–50%), human lung adenocarcinomas (15–24%), thyroid tumors (50%) and myeloid leukemia (30%) (Millis, N. E. et al.

(1995) *Cancer Res.* 55:1444; Chaubert, P. et al. (1994), *Am. J. Path.* 144:767; Bos, J. (1989) *Cancer Res.* 49:4682). Ras activation is also demonstrated by upstream mitogenic signaling elements, notably by tyrosine receptor kinases (RTKs). These upstream elements, if amplified or overexpressed, ultimately result in elevated Ras activity by the signal transduction activity of Ras. Examples of this include overexpression of PDGFR in certain forms of glioblastomas, as well as in c-erbB-2/neu in breast cancer (Levitzki, A. (1994) *Eur. J. Biochem.* 226:1; James, P. W., et al. (1994) *Oncogene* 9:3601; Bos, J. (1989) *Cancer Res.* 49:4682).

Current methods of treatment for neoplasia include surgery, chemotherapy and radiation. Surgery is typically used as the primary treatment for early stages of cancer; however, many tumors cannot be completely removed by surgical means. In addition, metastatic growth of neoplasms may prevent complete cure of cancer by surgery. Chemotherapy involves administration of compounds having antitumor activity, such as alkylating agents, antimetabolites, and antitumor antibiotics. The efficacy of chemotherapy is often limited by severe side effects, including nausea and vomiting, bone marrow depression, renal damage, and central nervous system depression. Radiation therapy relies on the greater ability of normal cells, in contrast with neoplastic cells, to repair themselves after treatment with radiation. Radiotherapy cannot be used to treat many neoplasms, however, because of the sensitivity of tissue surrounding the tumor. In addition, certain tumors have demonstrated resistance to radiotherapy and such may be dependent on oncogene or anti-oncogene status of the cell (Lee. J. M. et al. (1993) *PNAS* 90:5742–5746; Lowe. S. W. et al. (1994) *Science,* 266:807–810; Raybaud-Diogene. H. et al. (1997) *J. Clin. Oncology,* 15(3):1030–1038). In view of the drawbacks associated with the current means for treating neoplastic growth, the need still exists for improved methods for the treatment of most types of cancers.

SUMMARY OF THE INVENTION

The present invention pertains to a method of treating a ras-mediated proliferative disorder in a mammal selected from dogs, cats, sheep, goats, cattle, horses, pigs, humans and non-human primates, comprising administering to the proliferating cells an effective amount of one or more reoviruses in the absence of BCNU under conditions which result in substantial lysis of the proliferating cells. The reovirus may be a mammalian reovirus or an avian reovirus. The reovirus may be modified such that the outer capsid is removed, the virion is packaged in a liposome or micelle or the proteins of the outer capsid have been mutated. The reovirus can be administered in a single dose or in multiple doses. The proliferative disorder may be a neoplasm. Both solid and hematopoietic neoplasms can be targeted.

Also provided is a method of treating a ras-mediated neoplasm in a human, comprising administering to the neoplasm a reovirus in an amount sufficient to result in substantial oncolysis of the neoplastic cells. The reovirus may be administered by injection into or near a solid neoplasm.

Also provided is a method of inhibiting metastasis of a neoplasm in a mammal, comprising administering to the mammal a reovirus in an amount sufficient to result in substantial lysis of the neoplastic cells.

Also provided is a method of treating a suspected ras-mediated neoplasm in a mammal, comprising surgical removal of the substantially all of the neoplasm and administration of an effective amount of reovirus at or near to the surgical site resulting in oncolysis of any remaining neoplastic cells.

Also provided is a pharmaceutical composition comprising a reovirus, a chemotherapeutic agent and a pharmaceutically acceptable excipient with the proviso that the chemotherapeutic agent is not BCNU.

Also provided is a pharmaceutical composition comprising a modified reovirus and a pharmaceutically acceptable excipient.

The methods and pharmaceutical compositons of the invention provide an effective means to treat neoplasia, without the side effects associated with other forms of cancer therapy. Furthermore, because reovirus is not known to be associated with disease, any safety concerns associated with deliberate administration of a virus are minimized.

The foregoing and other objects, features and advantages of the invention will be apparent from the following more particular description of preferred embodiments of the invention, as illustrated in the accompanying drawings.

DETAILED DESCRIPTION OF THE INVENTION

Figure 1:
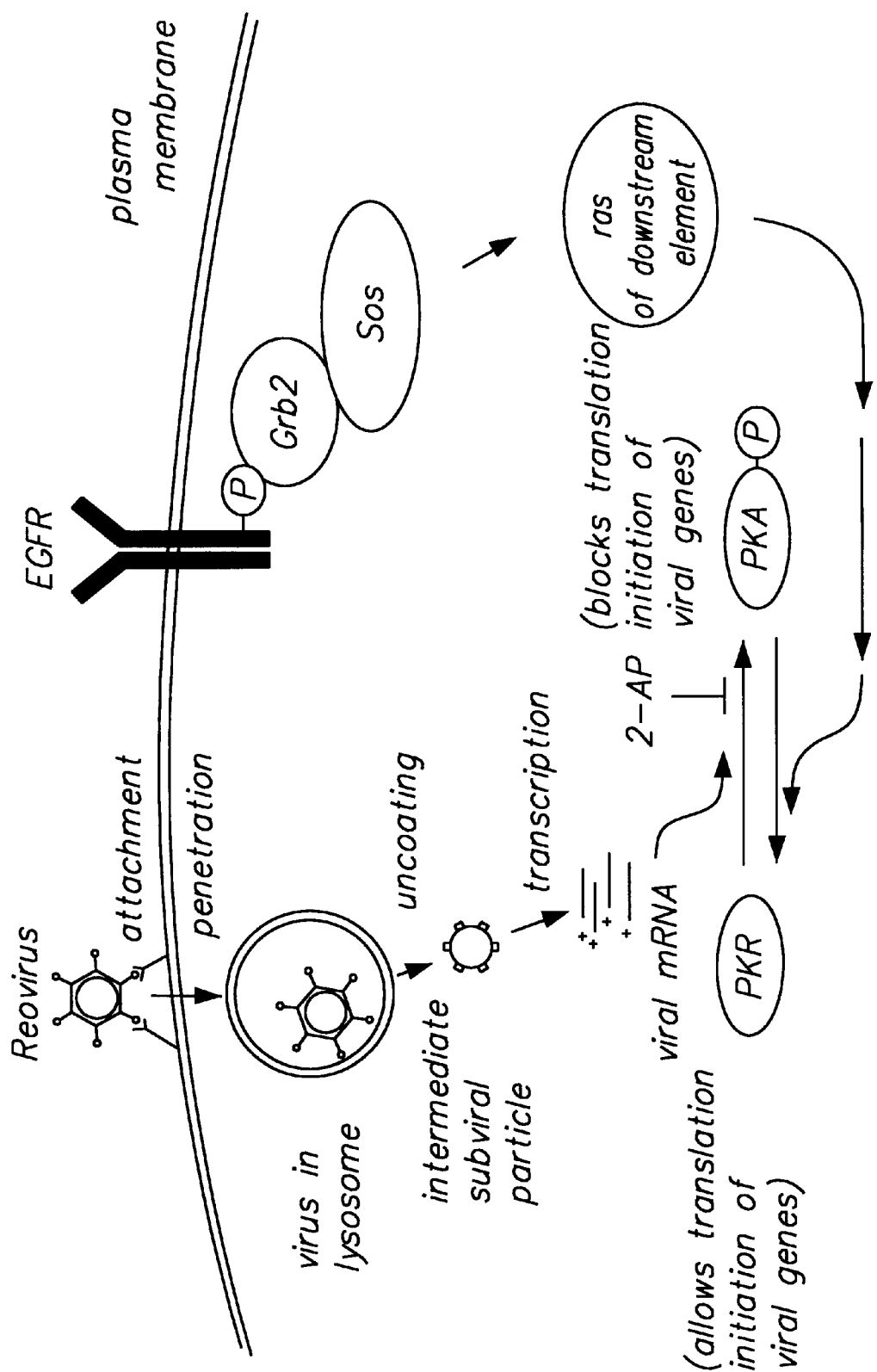
FIG. 1 is a depiction of the molecular basis of reovirus oncolysis, in which the reovirus usurps the host cell Ras signaling pathway.

The invention pertains to methods of treating a ras-mediated proliferative disorder in a mammal, by administering reovirus to the proliferating cells.

The name reovirus (Respiratory and enteric orphan virus) is a descriptive acronym suggesting that these viruses, although not associated with any known disease state in humans, can be isolated from both the respiratory and enteric tracts (Sabin, A. B. (1959), *Science* 130:966). The term "reovirus" refers to all viruses classified in the reovirus genus.

Reoviruses are viruses with a double-stranded, segmented RNA genome. The virions measure 60–80 nm in diameter and possess two concentric capsid shells, each of which is icosahedral. The genome consists of double-stranded RNA in 10–12 discrete segments with a total genome size of 16–27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (Sabin, A. B. (1959), *Science* 130:966; Fields, B. N. et al. (1996), *Fundamental Virology*, 3rd Edition, Lippincott-Raven; Rosen, L. (1960) *Am. J. Hyg.*71:242; Stanley, N. F. (1967) *Br. Med. Bull.* 23:150).

Although reovirus is not known to be associated with any particular disease, many people have been exposed to reovirus by the time they reach adulthood (i.e., fewer than 25% in children <5 years old, to greater than 50% in those 20–30 years old (Jackson G. G. and Muldoon R. L. (1973) *J. Infect. Dis.* 128:811; Stanley N. F. (1974) In: *Comparative Diagnosis of Viral Diseases*, edited by E. Kurstak and K. Kurstak, 385–421, Academic Press, New York).

For mammalian reoviruses, the cell surface recognition signal is sialic acid (Armstrong, G. D. et al. (1984), *Virology* 138:37; Gentsch, J. R. K. and Pacitti, A. F. (1985), *J. Virol.* 56:356; Paul R. W. et al. (1989) *Virology* 172:382–385) Due to the ubiquitous nature of sialic acid, reovirus binds efficiently to a multitude of cell lines and as such can potentially target many different tissues; however, there are significant differences in susceptibility to reovirus infection between cell lines.

As described herein, Applicants have discovered that cells which are resistant to reovirus infection became susceptible to reovirus infection when transformed by a gene in the Ras pathway. "Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription: while viral transcripts were produced, virus proteins were not expressed. Without being limited to a theory, it is thought that viral gene transcription in resistant cells correlated with phosphorylation of an approximately 65 kDa cell protein, determined to be double-stranded RNA-activated protein kinase (PKR), that was not observed in transformed cells. Phosphorylation of PKR lead to inhibition of translation. When phosphorylation was suppressed by 2-aminopurine, a known inhibitor of PKR, drastic enhancement of reovirus protein synthesis occurred in the untransformed cells. Furthermore, a severe combined immunodeficiency (SCID) mouse model in which tumors were created on both the right and left hind flanks revealed that reovirus significantly reduced tumor size when injected directly into the right-side tumor; in addition, significant reduction in tumor size was also noted on the left-side tumor which was not directly injected with reovirus, indicating that the oncolytic capacity of the reovirus was systemic as well as local.

These results indicated that reovirus uses the host cell's Ras pathway machinery to downregulate PKR and thus reproduce. FIG. 1 depicts the usurpation of the host cell Ras signalling pathway by reovirus. As shown in FIG. 1, for both untransformed (reovirus-resistant) and EGFR-, Sos-, or ras-transformed (reovirus-susceptible) cells, virus binding, internalization, uncoating, and early transcription of viral genes all proceed normally. In the case of untransformed cells, secondary structures on the early viral transcripts inevitably trigger the phosphorylation of PKR, thereby activating it, leading to the phosphorylation of the translation initiation factor eIF-$2\alpha$, and hence the inhibition of viral gene translation. In the case of EGFR-, Sos-, or ras-transformed cells, the PKR phosphorylation step is prevented or reversed by Ras or one of its downstream elements, thereby allowing viral gene translation to ensue. The action of Ras (or a downstream element) can be mimicked by the use of 2-aminopurine (2-AP), which promotes viral gene translation (and hence reovirus infection) in untransformed cells by blocking PKR phosphorylation.

The implantation of human tumor cells into SCID mice is recognized as a well known model system for testing the effectiveness of various anti-tumor agents in humans. It has previously been shown that pharmaceuticals effective against human tumors implanted into SCID mice are predictive of their effectiveness against the same tumors in humans.

Based upon these discoveries, Applicants have developed methods for treating ras-mediated proliferative disorders in mammals. Representative mammals include dogs, cats, sheep, goats, cattle, horses, pigs, non-human primates, and humans. In a preferred embodiment, the mammal is a human.

In the methods of the invention, reovirus is administered to ras-mediated proliferating cells in the individual mammal. Representative types of human reovirus that can be used include type 1 (e.g., strain Lang or T1L); type 2 (e.g., strain Jones or T2J); and type 3 (e.g., strain Dearing or strain Abney, T3D or T3A); other strains of reovirus can also be used. In a preferred embodiment, the reovirus is human reovirus serotype 3, more preferably the reovirus is human reovirus serotype 3, strain Dearing. Alternatively, the reovirus can be a non-human mammalian reovirus (e.g., non-human primate reovirus, such as baboon reovirus; equine; or canine reovirus), or a non-mammalian reovirus (e.g., avian reovirus). A combination of different serotypes and/or different strains of reovirus, such as reovirus from different species of animal, can be used.

The reovirus may be naturally occurring or modified. The reovirus is "naturally-occurring": when it can be isolated from a source in nature and has not been intentionally modified by humans in the laboratory. For example, the reovirus can be from a "field source": that is, from a human patient.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, "Protease cleavage of reovirus capsid protein mu1 and mu1C is blocked by alkyl sulfate detergents, yielding a new type of infectious subvirion particle", *J. of Virology* 72(1):467–75 (1998)) to reduce or prevent an immune response from a mammal which has developed immunity to the reovirus. For example, the virion may be treated with chymotrypsin in the presence of micelle forming concentrations of alkyl sulfate detergents to generate a new infectious subvirion particle.

The reovirus may be a recombinant reovirus from two or more types of reoviruses with differing pathogenic phenotypes such that it contains different antigenic determinants thereby reducing or preventing an immune response by a mammal previously exposed to a reovirus subtype. Such recombinant virions can be generated by co-infection of mammalian cells with different subtypes of reovirus with the resulting resorting and incorporation of different subtype coat proteins into the resulting virion capsids.

The reovirus may be modified by incorporation of mutated coat proteins, such as for example σ1, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein.

Expression of the mutated protein in reovirus infected mammalian cells in vitro such as COS1 cells will result in the incorporation of the mutated protein into the reovirus virion particle (Turner and Duncan, "Site directed mutagenesis of the C-terminal portion of reovirus protein signal: evidence for a conformation-dependent receptor binding domain" *Virology* 186(1):219–27 (1992); Duncan et al., "Conformational and functional analysis of the C-terminal globular head of the reovirus cell attachment protein" *Virology* 182(2):810–9 (1991); Mah et al., "The N-terminal quarter of reovirus cell attachment protein sigma 1 possesses intrinsic virion-anchoring function" *Virology* 179(1):95–103 (1990)).

The reovirus is preferably a reovirus modified to reduce or eliminate an immune reaction to the reovirus. Such modified reovirus are termed "immunoprotected reovirus". Such modifications could include packaging of the reovirus in a liposome, a micelle or other vehicle to mask the reovirus from the mammals immune system. Alternatively, the outer capsid of the reovirus virion particle may be removed since the proteins present in the outer capsid are the major determinant of the host humoral and cellular responses.

A "proliferative disorder" is any cellular disorder in which the cells proliferate more rapidly than normal tissue growth. Thus a "proliferating cell" is a cell that is proliferating more rapidly than normal cells. The proliferative disorder, includes but is not limited to neoplasms. A neoplasm is an abnormal tissue growth, generally forming a distinct mass, that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a "neoplasm", also referred to as a "tumor", is intended to encompass hematopoietic neoplasms as well as solid neoplasms. Other proliferative disorders include, but are not limited to neurofibromatosis.

At least some of the cells of the proliferative disorder have a mutation in which the Ras gene (or an element of the Ras signaling pathway) is activated, either directly (e.g., by an activating mutation in Ras) or indirectly (e.g., by activation of an upstream element in the Ras pathway). Activation of an upstream element in the Ras pathway includes, for example, transformation with epidermal growth factor receptor (EGFR) or Sos. A proliferative disorder that results, at least in part, by the activation of Ras, an upstream element of Ras, or an element in the Ras signalling pathway is referred to herein as a "Ras-mediated proliferative disorder".

One neoplasm that is particularly susceptible to treatment by the methods of the invention is pancreatic cancer, because of the prevalence of Ras-mediated neoplasms associated with pancreatic cancer. Other neoplasms that are particularly susceptible to treatment by the methods of the invention include breast cancer, central nervous system cancer (e.g., neuroblastoma and glioblastoma), peripheral nervous system cancer, lung cancer, prostate cancer, colorectal cancer, thyroid cancer, renal cancer, adrenal cancer, liver cancer, lymphoma and leukemia. One proliferative disorder that is particularly susceptible to treatment by the methods of this invention include neurofibromatosis 1 because of the activation of the ras pathway.

"Administration to a proliferating cell or neoplasm" indicates that the reovirus is administered in a manner so that it contacts the proliferating cells or cells of the neoplasm (also referred to herein as "neoplastic cells"). The route by which the reovirus is administered, as well as the formulation, carrier or vehicle, will depend on the location as well as the type of the neoplasm. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases or brain tumors, the reovirus is administered in a manner such that it can be transported systemically through the body of the mammal and thereby reach the neoplasm (e.g., intrathecally, intravenously or intramuscularly). Alternatively, the reovirus can be administered directly to a single solid neoplasm, where it then is carried systemically through the body to metastases. The reovirus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

Reovirus can be administered systemically to mammals which are immune compromised or which have not developed immunity to the reovirus epitopes. In such cases, reovirus administered systemically, i.e. by intraveneous injection, will contact the proliferating cells resulting in lysis of the cells.

Immunocompetent mammals previously exposed to a reovirus subtype may developed humoral and/or cellular immunity to that reovirus subtype. Nevertheless, it has been found that direct injection of the reovirus into a solid tumor in immunocompetent mammals will result in the lysis of the neoplastic cells.

On the other hand, when the reovirus is administered systemically to immunocompetent mammals, the mammals may produce an immune response to the reovirus. Such an immune response may be avoided if the reovirus is of a subtype to which the mammal has not developed immunity, or the reovirus has been modified as previously described herein such that it is immunoprotected, for example, by protease digestion of the outer capsid or packaging in a micelle.

Alternatively, it is contemplated that the immunocompetency of the mammal against the reovirus may be suppressed either by the co-administration of pharmaceuticals known in the art to suppress the immune system in general (Cuff et al., "Enteric reovirus infection as a probe to study immunotoxicity of the gastrointestinal tract" *Toxicological Sciences* 42(2):99–108 (1998)) or alternatively the administration of anti-antireovirus antibodies. The humoral immunity of the mammal against reovirus may also be temporarily reduced or suppressed by plasmaphoresis of the mammals blood to remove the anti-reovirus antibodies. The humoral immunity of the mammal against reovirus may additionally be temporarily reduced or suppressed by the intraveneous administration of non-specific immunoglobulin to the mammal.

It is contemplated that the reovirus may be administered to immunocompetent mammals immunized against the reovirus in conjunction with the administration of anti-antireovirus antibodies. "Anti-antireovirus antibodies" are antibodies directed against anti-reovirus antibodies. Such antibodies can be made by methods known in the art. See for example "Antibodies: A laboratory manual" E. Harlow and D. Lane, Cold Spring Harbor Laboratory (1988). Such anti-antireovirus antibodies may be administered prior to, at the same time or shortly after the administration of the reovirus. Preferably an effective amount of the anti-antireovirus antibodies are administered in sufficient time to reduce or eliminate an immune response by the mammal to the administered reovirus.

The term "substantial lysis" means at least 10% of the proliferating cells are lysed, more preferably of at least 50% and most preferably of at least 75% of the cells are lysed. The percentage of lysis can be determined for tumor cells by measuring the reduction in the size of the tumor in the mammal or the lysis of the tumor cells in vitro.

A "mammal suspected of having a proliferative disorder" means that the mammal may have a proliferative disorder or tumor or has been diagnosed with a proliferative disorder or tumor or has been previously diagnosed with a proliferative disorder or tumor, the tumor or substantially all of the tumor has been surgically removed and the mammal is suspected of harboring some residual tumor cells.

This invention also includes pharmaceutical compositions which contain, as the active ingredient, one or more of the reoviruses associated with "pharmaceutically acceptable carriers or excipients". In making the compositions of this invention, the active ingredient/reovirus is usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient.

Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient/reovirus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former.

The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The reovirus or the pharmaceutical composition comprising the reovirus may be packaged into convenient kits providing the necessary materials packaged into suitable containers. It is contemplated the kits may also include chemotherapeutic agents and/or anti-antireovirus antibody.

The reovirus is administered in an amount that is sufficient to treat the proliferative disorder (e.g., an "effective amount"). A proliferative disorder is "treated" when administration of reovirus to the proliferating cells effects lysis of the proliferating cells. This may result in a reduction in size of the neoplasm, or in a complete elimination of the neoplasm. The reduction in size of the neoplasm, or elimination of the neoplasm, is generally caused by lysis of neoplastic cells ("oncolysis") by the reovirus. Preferably the effective amount is that amount able to inhibit tumor cell growth. Preferably the effective amount is from about 1.0 pfu/kg body weight to about $10^{15}$ pfu/kg body weight, more preferably from about $10^2$ pfu/kg body weight to about $10^{13}$ pfu/kg body weight. For example, for treatment of a human, approximately $10^2$ to $10^{17}$ plaque forming units (PFU) of reovirus can be used, depending on the type, size and number of tumors present. The effective amount will be determined on an individual basis and may be based, at least in part, on consideration of the type of reovirus; the chosen route of administration; the individual's size, age, gender; the severity of the patient's symptoms; the size and other characteristics of the neoplasm; and the like. The course of therapy may last from several days to several months or until diminution of the disease is achieved.

The reovirus can be administered in a single dose, or multiple doses (i.e., more than one dose). The multiple doses can be administered concurrently, or consecutively (e.g., over a period of days or weeks). The reovirus can also be administered to more than one neoplasm in the same individual.

The compositions are preferably formulated in a unit dosage form, each dosage containing from about $10^2$ pfus to about $10^{13}$ pfus of the reovirus. The term "unit dosage forms" refers to physically discrete units suitable as unitary dosages for human subjects and other mammals, each unit containing a predetermined quantity of reovirus calculated to produce the desired therapeutic effect, in association with a suitable pharmaceutical excipient.

It has been found that the reovirus is effective for the treatment of solid neoplasms in immunocompetent mammals. Administration of unmodified reovirus directly to the neoplasm results in oncolysis of the neoplastic cells and reduction in the size of the tumor.

It is contemplated that the reovirus may be administered in conjunction with surgery or removal of the neoplasm. Therefore, provided herewith are methods for the treatment of a solid neoplasm comprising surgical removal of the neoplasm and administration of a reovirus at or near to the site of the neoplasm.

It is contemplated that the reovirus may be administered in conjunction with or in addition to radiation therapy.

It is further contemplated that the reovirus of the present invention may be administered in conjunction with or in addition to known anticancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etopside, pregnasome, platinum compounds such as carboplatin and cisplatin, taxanes such as taxol and taxotere, hormone therapies such as tamoxifen and anti-estrogens, interferons, aromatase inhibitors, progestational agents and LHRH analogs.

Preferably the reovirus is administered in the absence of 1,3-bis(2-chloroethyl)-1-nitrosourea (BCNU). For example, the 1,3-bis(2-chloroethyl)-1-nitrosourea (BCNU) is not administered to the mammal either before, during or after the mammal receives the reovirus.

The reovirus of the present invention have been found to reduce the growth of tumors that are metastatic. In an embodiment of the invention, a method is provided for reducing the growth of metastastic tumors in a mammal comprising administering an effective amount of a reovirus to the mammal.

Utility

The reoviruses of the present invention may be used for a variety of purposes. They may be used in methods for treating ras-mediated proliferative disorders in a mammal. The reovirus may be used to reduce or eliminate neoplasms. They may be used in methods for treating metastases. They may be used in conjunction with known treatments for cancer including surgery, chemotherapy and radiation.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning.

| | |
|---|---|
| μM = | micromolar |
| mM = | millimolar |
| M = | molar |
| ml = | milliliter |
| μl = | microliter |
| mg = | milligram |
| μg = | microgram |
| PAGE = | polyacrylamide gel electrophoresis |
| rpm = | revolutions per minute |
| FBS = | fetal bovine serum |
| DTT = | dithiothrietol |
| SDS = | sodium dodecyl sulfate |
| PBS = | phosphate buffered saline |
| DMEM = | Dulbecco's modified Eagle's medium |
| α-MEM = | α-modified Eagle's medium |
| β-ME = | β-mercaptoethanol |
| MOI = | multiplicity of infection |
| PFU = | plaque forming units |
| MAPK = | MAP kinase |
| phosph-MAPK = | phosphorylated-MAP kinase |
| HRP = | horseradish-peroxidase |

-continued

| | |
|---|---|
| PKR = | double-stranded RNA activated protein kinase |
| RT-PCR = | reverse transcriptase-polymerase chain reaction |
| GAPDH = | glyceraldehyde-3-phosphate dehydrogenase |
| EGFR = | epidermal growth factor receptors |
| MEK kinase = | mitogen-activated extracellular signal-regulated kinase |
| DMSO = | dimethylsulfoxide |
| SCID = | severe combined immunodeficiency |

General Methods

Cells and Virus

Parental NIH-3T3 and NIH-3T3 cells transfected with the Harvey-ras (H-ras) and EJ-ras oncogenes were a generous gift of Dr. Douglas Faller (Boston University School of Medicine). NIH-3T3 cells along with their Sos-transformed counterparts (designated TNIH#5) were a generous gift of Dr. Michael Karin (University of California, San Diego). Dr. H. -J. Kung (Case Western Reserve University) kindly donated parental NIH-3T3 cells along with NIH-3T3 cells transfected with the v-erbB oncogene (designated THC-11). 2H1 cells, a derivative of the C3H 10T½ murine fibroblast line, containing the Harvey-ras gene under the transcriptional control of the mouse metallotionein-I promoter were obtained from Dr. Nobumichi Hozumi (Mount Sinai Hospital Research Institute). These 2H1 cells are conditional ras transformant that express the H-ras oncogene in the presence of 50 $\mu$M $ZnSO_4$. All cell lines were grown in Dulbecco's modified Eagle's medium (DMEM) containing 10% fetal bovine serum (FBS).

The NIH-3T3 tet-myc cells were obtained from Dr. R. N. Johnston (University of Calgary) and were grown in DMEM containing 10% heat-inactivated FBS and antibiotics in the presence or absence of 2 $\mu$g/ml tetracycline (Helbing, C. C. et al., *Cancer Res.* 57:1255–1258 (1997)). In the presence of tetracycline, expression of the human c-myc gene is repressed. Removal of tetracycline results in the elevation of expression of c-myc by up to 100-fold in these cells, which also display a transformed phenotype.

The $PKR^{+/+}$ and $PKR^{0/0}$ mouse embryo fibroblasts (MEFs) were obtained from Dr. B. R. G. Williams (the Cleveland Clinic Foundation) and were grown in $\alpha$-MEM containing fetal bovine serum and antibiotics as previously described (Yang, Y. L. et al. *EMBO J.* 14:6095–6106 (1995); Der, S. D. et al., *Proc. Natl. Acad. Sci.* USA 94:3279–3283 (1997)).

The Dearing strain of reovirus serotype 3 used in these studies was propagated in suspension cultures of L cells and purified according to Smith (Smith, R. E. et al., (1969) *Virology*, 39:791–800) with the exception that $\beta$-mercaptoethanol ($\beta$-ME) was omitted from the extraction buffer. Reovirus labelled with [$^{35}$S]methionine was grown and purified as described by McRae and Joklik (McRae, M. A. and Joklik, W. K., (1978) *Virology*, 89:578–593). The particle/PFU ratio for purified reovirus was typically 100/1.

Immunofluorescent Analysis of Reovirus Infection

For the immunofluorescent studies the NIH-3T3, TNIH#5, H-ras, EJ-ras, 2H1 ($\pm ZnSO_4$), and THC-11 cells were grown on coverslips, and infected with reovirus at a multiplicity of infection (MOI) of ~10 PFU cell or mock-infected by application of the carrier agent (phosphate-buffered saline, PBS) to the cells in an identical fashion as the administration of virus to the cells. At 48 hours postinfection, cells were fixed in an ethanol/acetic acid (20/1) mixture for 5 minutes, then rehydrated by sequential washes in 75%, 50% and 25% ethanol, followed by four washes with phosphate-buffered saline (PBS). The fixed and rehydrated cells were then exposed to the primary antibody (rabbit polyclonal anti-reovirus type 3 serum diluted 1/100 in PBS) [antiserum prepared by injection of rabbits with reovirus serotype 3 in Freund's complete adjuvant, and subsequent bleedings] for 2 hours at room temperature. Following three washes with PBS, the cells were exposed to the secondary antibody [goat anti-rabbit IgG (whole molecule)-fluorescein isothiocyanate conjugate (FITC) [Sigma ImmunoChemicals F-0382] diluted 1/100 in PBS containing 10% goat serum and 0.005% Evan's Blue] for 1 hour at room temperature. Finally, the fixed and treated cells were washed three more times with PBS and then once with double-distilled water, dried and mounted on slides in 90% glycerol containing 0.1% phenylenediamine, and viewed with a Zeiss Axiophot microscope on which Carl Zeiss camera was mounted (the magnification for all pictures was 200×).

Detection of MAP Kinase (ERK) Activity

The PhosphoPlus p44/42 MAP kinase (Thr202/Tyr204) Antibody kit (New England Biolabs) was used for the detection of MAP kinase in cell lysates according to the manufacturer's instructions. Briefly, subconfluent monolayer cultures were lysed with the recommended SDS-containing sample buffer, and subjected to SDS-PAGE, followed by electroblotting onto nitrocellulose paper. The membrane was then probed with the primary antibody (anti-total MAPK or anti-phospho-MAPK), followed by the horseradish peroxidase (HRP)-conjugated secondary antibody as described in the manufacturer's instruction manual.

Radiolabelling of Reovirus-Infected Cells and Preparation of Lysates

Confluent monolayers of NIH-3T3, TNIH#5, H-ras, EJ-ras, 2H1 ($\pm ZnSO_4$), and THC-11 cells were infected with reovirus (MOI~10 PFU/cell). At 12 hours postinfection, the media was replaced with methionine-free DMEM containing 10% dialyzed FBS and 0.1 mCi/ml [$^{35}$S]methionine. After further incubation for 36 hours at 37° C., the cells were washed in phosphate-buffered saline (PBS) and lysed in the same buffer containing 1% Triton X-100, 0.5% sodium deoxycholate and 1 mM EDTA. The nuclei were then removed by low speed centrifugation and the supernatants were stored at −70° C. until use.

Preparation of Cytoplasmic Extracts for In Vitro Kinase Assays

Confluent monolayers of the various cell lines were grown on 96 well cell culture plates. At the appropriate time postinfection the media was aspirated off and the cells were lysed with a buffer containing 20 mM HEPES [pH 7.4], 120 mM KCl, 5 mM $MgCl_2$, 1 mM dithiothreitol, 0.5% Nonidet P-40, 2 $\mu$g/ml leupeptin, and 50 $\mu$g/ml aprotinin. The nuclei were then removed by low-speed centrifugation and the supernatants were stored at −70° C. until use.

Cytoplasmic extracts were normalized for protein concentrations before use by the Bio-Rad protein microassay method. Each in vitro kinase reaction contained 20 $\mu$l of cell extract, 7.5 $\mu$l of reaction buffer (20 mM HEPES [pH 7.4], 120 mM KCl, 5 mM $MgCl_2$, 1 mM dithiothreitol, and 10% glycerol) and 7.0 $\mu$l of ATP mixture (1.0 $\mu$Ci[$\gamma$-$^{32}$P]ATP in 7 $\mu$l of reaction buffer), and was incubated for 30 minutes at 37° C. (Mundschau, L. J.,and Faller, D. V., *J. Biol. Chem.*, 267:23092–23098 (1992)). Immediately after incubation the labelled extracts were either boiled in Laemmli SDS-sample buffer or were either precipitated with agarose-poly(I)poly (C) beads or immunoprecipitated with an anti-PKR antibody.

Agarose poly(I)poly(C) Precipitation

To each in vitro kinase reaction mixture, 30 $\mu$l of a 50% $\mu$g poly(I)poly(C) Type 6 slurry (Pharmacia LKB Biotechnology) was added, and the mixture was incubated at 4° C. for 1 h. The Ag poly(I)poly(C) beads with the absorbed, labelled proteins were then washed four times with wash buffer (20 mM HEPES [7.5 pH], 90 mM KCl, 0.1 mM EDTA, 2 mM dithiothreitol, 10% glycerol) at room temperature and mixed with 2X Laemmli SDS sample buffer. The beads were then boiled for 5 min, and the released proteins were analyzed by SDS-PAGE.

Polymerase Chain Reaction

Cells at various times postinfection were harvested and resuspended in ice cold TNE (10 mM Tris [pH 7.8], 150 mM NaCl, 1 mM EDTA) to which NP-40 was then added to a final concentration of 1%. After 5 minutes, the nuclei were pelleted and RNA was extracted from the supernatant using the phenol:chloroform procedure. Equal amounts of total cellular RNA from each sample were then subjected to RT-PCR (Wong, H., et al., (1994) *Anal. Biochem.*, 223:251–258) using random hexanucleotide primers (Pharmacia) and RTase (GIBCO-BRL) according to the manufacturers' protocol.

The cDNA's from the RT-PCR step were then subjected to selective amplification of reovirus cDNA using appropriate primers that amplify a predicted 116 bp fragment. These primer sequences were derived from the S1 sequence determined previously (Nagata, L., et al., (1984) *Nucleic Acids Res.*, 12:8699–8710). The GAPDH primers of Wong, H., et al., (1994) *Anal. Biochem.*, 223:251–258 were used to amplify a predicted 306 bp GAPDH fragment which served as a PCR and gel loading control.

Selective amplification of the s1 and GAPDH cDNA's was performed using Taq DNA polymerase (GIBCO-BRL) according to the manufacturers' protocol using a Perkin Elmer Gene Amp PCR system 9600. PCR was carried out for 28 cycles with each consisting of a denaturing step for 30 seconds at 97° C., annealing step for 45 seconds at 55° C., and polymerization step for 60 seconds at 72° C. PCR products were analyzed by electrophoresis through an ethidium bromide-impregnated TAE-2% agarose gel and photographed under ultra-violet illumination with Polaroid 57 film.

Immunoprecipitation and SDS-PAGE Analysis

Immunoprecipitation of $^{35}$S-labelled reovirus-infected cell lysates with anti-reovirus serotype 3 serum was carried out as previously described (Lee, P. W. K. et al. (1981) *Virology*, 108:134–146). Immunoprecipitation of $^{32}$P-labelled cell lysates with an anti-PKR antibody (from Dr. Michael Mathews, Cold Spring Harbor) was similarly carried out. Immunoprecipitates were analyzed by continuous SDS-PAGE according to the protocol of Laemmli (Laemmli, U.K., 1970) *Nature*, 227:680–685).

Example 1

Activated Intermediates in the Ras Signalling Pathway Augment Reovirus Infection Efficiency It was previously shown that 3T3 cells and their derivatives lacking epidermal growth factor receptors (EGFR) are poorly infectible by reovirus, whereas the same cells transformed with either EGFR or v-erb B are highly susceptible as determined by cytopathic effects, viral protein synthesis, and virus output (Strong, J. E. et al.,(1993) *Virology*, 197:405411; Strong, J. E. and Lee, P. W. K., (1996) *J. Virol.*, 70:612–616).

To determine whether downstream mediators of the EGFR signal transduction pathway may be involved, a number of different NIH 3T3-derived, transformed with constitutively activated oncogenes downstream of the EGFR, were assayed for relative susceptibility to reovirus infection. Of particular interest were intermediates in the ras signalling pathway (reviewed by Barbacid, M., *Annu. Rev. Biochem.*, 56:779–827 (1987); Cahill, M. A., et al., *Curr. Biol.*, 6:16–19 (1996). To investigate the Ras signalling pathway, NIH 3T3 parental cell lines and NIH 3T3 lines transfected with activated versions of Sos (Aronheim, A., et al., (1994) *Cell*, 78:949–961) or ras (Mundschau, L. J. and Faller, D. V., (1992) *J. Biol. Chem.*, 267:23092–23098) oncogenes were exposed to reovirus, and their capacity to promote viral protein synthesis was compared.

Detection of viral proteins was initially carried out using indirect immunofluorescent microscopy as described above. The results indicated that whereas the NIH 3T3 cells adopted a typically flattened, spread-out morphology with marked contact inhibition, the transformed cells all grew as spindle-shaped cells with much less contact inhibition. On comparing the uninfected parental cell lines with the various transformed cell lines, it was apparent that the morphology of the cells was quite distinct upon transformation. Upon challenge with reovirus, it became clear that parental NIH 3T3 line was poorly infectible (<5%), regardless of the source of the parental NIH 3T3 line. In contrast, the transfected cell lines each demonstrated relatively pronounced immunofluorescence by 48 hours postinfection (data not shown).

To demonstrate that viral protein synthesis was more efficient in the Sos- or Ras-transformed cell lines, cells were continuously labeled with [$^{35}$S]-methionine from 12 to 48 hr postinfection and the proteins were analyzed by sodium dodecyl sulfate-polyacrylamide gel electrophoresis (SDS-PAGE), as described above.

The results showed clearly that the levels of viral protein synthesis were significantly higher in the Sos- or Ras-transformed cells than in parental NIH 3T3 cells. The identities of the viral bands were confirmed by immunoprecipitation of the labeled proteins with polyclonal anti-reovirus antibodies. Since the uninfected NIH 3T3 cells and their transformed counterparts displayed comparable levels of cellular protein synthesis and doubling times (data not shown), the observed difference in the level of viral protein synthesis could not be due to intrinsic differences in growth rates or translation efficiencies for these cell lines.

The long-term fate of infected NIH-3T3 cells was followed by passaging these cells for at least 4 weeks. They grew normally and appeared healthy, with no sign of lytic or persistent infection; no virus could be detected in the medium after this time (data not shown).

Example 2

Enhanced Infectibility Conferred by Activated Oncogenes is Not Due to Long-term Transformation or the Generalized Transformed State of the Cell To determine whether the differences in susceptibility may be the result of long-term effects of transformation, or the result of the activated oncogene itself, a cell line expressing a zinc-inducible cellular Harvey-ras (c-H-ras) gene was tested for susceptibility to reovirus infectibility, as described above. These cells, called 2H1, were derived from the C3H 10T½ cell line which is poorly infectible by reovirus (data not shown), and carry the c-H-ras gene under the control of the mouse metallothionine-I promoter (Trimble, W. S. et al. (1986) *Nature*, 321:782–784).

Cells were either mock-treated or pretreated with 50 μM ZnSO$_4$ 18 hours prior to infection or mock-infection (administration of carrier agent), followed by indirect immunofluorescent analysis of these cells at 48 hours postinfection or mock-infection.

The results (not shown) demonstrated that uninduced cells were poorly infectible (<5%) whereas those induced for only 18 hours were much more susceptible (>40%). Enhanced viral protein synthesis in the Zn-induced 2H1 cells was further confirmed by metabolic labeling of the cells with [$^{35}$S]methionine followed by SDS-PAGE analysis of virus-specific proteins (not shown).

Based on these observations, the augmentation of reovirus infection efficiency in the transformed cells is a direct result of the activated oncogene product(s), and not due to other factors such as aneuploidy often associated with long-term transformation, or other accumulated mutations that may be acquired under a chronically transformed state (e.g., p53 or myc activation).

To show further that susceptibility to reovirus infection is not a result of transformation per se (i.e., a result of the transformed state of the host cell), NIH-3T3 cells containing a tetracycline-controlled human c-myc gene (tet-myc cells) were examined (Helbing, C. C. et al., Cancer Res. 57:1255–1258 (1997)). These cells normally are maintained in tetracycline (2 μg/ml) which represses the expression of c-myc. Removal of tetracycline under normal growth conditions (10% fetal bovine serum) leads to accumulation of the c-Myc protein and the cells display a transformed phenotype. We found that these cells were unable to support virus growth either in the presence or in the absence of tetracycline (data not shown), suggesting that susceptibility to reovirus infection is not due to the general transformed state of the host cell, but rather requires specific transformation by elements of the Ras signaling pathway.

A good indicator of activation of the Ras signaling pathway is the activation of the MAP kinases ERK1 and ERK2 (for a review, see Robinson, M. J. and Cobb, M. H., Curr. Opin. Cell Biol. 9:180–186 (1997)). In this regard, it was found that, compared with untransformed cells, Ras-transformed cells have a significantly higher ERK½ activity (data not shown). Furthermore, an examination of a number of human cancer cell lines has revealed an excellent correlation between the level of ERK½ activity and susceptibility to reovirus infection (data not shown), although ERK½ itself does not appear to play any role in it. Mouse L cells and human HeLa cells, in which reovirus grows very well, both manifest high ERK½ activity (data not shown).

Example 3

Viral Transcripts are Generated but Not Translated in Reovirus-Resistant NIH 3T3 Cells The step at which reovirus infection is blocked in nonsusceptible NIH 3T3 cells was also identified. Because virus binding and virus internalization for nonsusceptible cells were comparable to those observed for susceptible cells (Strong, J. E. et al., (1993) Virology, 197:405–411), the transcription of viral genes was investigated.

The relative amounts of reovirus S1 transcripts generated in NIH 3T3 cells and the Ras-transformed cells during the first 12 hours of infection were compared after amplification of these transcripts by polymerase chain reaction (PCR), as described above. The results demonstrated that the rates of accumulation of S1 transcripts in the two cell lines were similar, at least up to 12 hours postinfection. Similar data were obtained when rates of accumulation of other reovirus transcripts were compared (data not shown). These results demonstrate that infection block in nonsusceptible cells is not at the level of transcription of viral genes, but rather, at the level of translation of the transcripts.

At later times, the level of viral transcripts present in untransformed NIH-3T3 cells decreased significantly whereas transcripts in transformed cells continued to accumulate (data not shown). The inability of these transcripts to be translated in NIH-3T3 cells probably contributed to their degradation. As expected, the level of viral transcripts in infected L cells was at least comparable with that in infected Ras-transformed cells (data not shown).

Example 4

A 65 kDa Protein is Phosphorylated in Reovirus-treated NIH 3T3 Cells but Not in Reovirus-infected Transformed Cells Because viral transcripts were generated, but not translated, in NIH 3T3 cells, it was investigated whether the double-stranded RNA (dsRNA)-activated protein kinase, PKR, is activated (phosphorylated) in these cells (for example, by S1 mRNA transcripts which have been shown to be potent activators of PKR (Bischoff, J. R. and Samuel, C. E., (1989) Virology, 172:106–115), which in turn leads to inhibition of translation of viral genes. The corollary of such a scenario would be that in the case of the transformed cells, this activation is prevented, allowing viral protein synthesis to ensue.

NIH 3T3 cells and v-erbB- or Ras-transformed cells (designated THC-11 and H-ras, respectively) were treated with reovirus (i.e., infected) or mock-infected (as above), and at 48 hours post treatment, subjected to in vitro kinase reactions, followed by autoradiographic analysis as described above.

The results clearly demonstrated that there was a distinct phosphoprotein migrating at approximately 65 kDa, the expected size of PKR, only in the NIH 3T3 cells and only after exposure to reovirus. This protein was not labeled in the lysates of either the uninfected transformed cell lines or the infected transformed cell lines. Instead, a protein migrating at approximately 100 kDa was found to be labeled in the transformed cell lines after viral infection. This protein was absent in either the preinfection or the postinfection lysates of the NIH 3T3 cell line, and was not a reovirus protein because it did not react with an anti-reovirus serum that precipitated all reovirus proteins (data not shown). A similar 100 kDa protein was also found to be $^{32}$P-labeled in in vitro kinase reactions of postinfection lysates of the Sos-transformed cell lines (data not shown).

That intermediates in the Ras signalling pathway were responsible for the lack of phosphorylation of the 65 kDa protein was further confirmed by the use of the 2H1 cells which contain a Zn-inducible Ras oncogene. Uninduced 2H1 cells(relatively resistant to reovirus infection, as shown above), were capable of producing the 65 kDa phosphoprotein only after exposure to virus. However, 2H1 cells subjected to Zn-induction of the H-Ras oncogene showed significant impairment of the production of this phosphoprotein. This impairment coincided with the enhancement of viral synthesis. These results therefore eliminated the possibility that the induction of the 65 kDa phosphoprotein was an NIH 3T3-specific event, and clearly established the role of Ras in preventing (or reversing) induction of the production of this phosphoprotein. The Zn-induced 2H1 cells did not produce the 100 kDa phosphoprotein seen in the infected, chronically transformed H-Ras cells.

Example 5

Induction of Phosphorylation of the 65 kDa Protein Requires Active Viral Transcription Since production of the 65 kDa phosphoprotein occurred only in cells that were resistant to reovirus infection, and only after the cells were exposed to reovirus, it was investigated whether active viral transcription was required for production of the 68 kDa phosphoprotein. Reovirus was UV-treated to inactivate its genome prior to administration of the reovirus to NIH 3T3 cells. For UV-treatment, reovirus was suspended in DMEM to a concentration of approximately $4 \times 10^8$ PFU/mL and exposed to short-wave (254 nm) UV light for 20 minutes. UV-inactivated virus were non-infectious as determined by lack of cytopathic effects on mouse L-929 fibroblasts and lack of viral protein synthesis by methods of [$^{35}$S]-methionine labelling as previously described. Such UV treatment abolished viral gene transcription, as analyzed by PCR, and hence viral infectivity (data not shown). The cells were then incubated for 48 hours, and lysates were prepared and subjected to in vitro $^{32}$P-labeling as before. The results showed that NIH 3T3 cells infected with untreated reovirus produced a prominent 65 kDa $^{32}$P-labelled band not found in uninfected cells. Cells exposed to UV-treated reovirus behaved similarly to the uninfected control cells, manifesting little phosphorylation of the 65 kDa protein. Thus, induction of the phosphorylation of the 65 kDa phosphoprotein is not due to dsRNA present in the input reovirus; rather, it requires de novo transcription of the viral genes, consistent with the identification of the 65 kDa phosphoprotein as PKR.

Example 6

Identification of the 65 kDa Phosphoprotein as PKR

To determine whether the 65 kDa phosphoprotein was PKR, a dsRNA binding experiment was carried out in which poly(I)-poly(c) agarose beads were added to $^{32}$P-labeled lysates, as described above. After incubation for 30 minutes at 4° C., the beads were washed, and bound proteins were released and analyzed by SDS-PAGE. The results showed that the 65 kDa phosphoprotein produced in the postinfection NIH 3T3 cell lysates was capable of binding to dsRNA; such binding is a well-recognized characteristic of PKR. In contrast, the 100 kDa phosphoprotein detected in the infected H-ras-transformed cell line did not bind to the Poly(I)-poly(c) agarose. The 65 kDa phosphoprotein was also immunoprecipitable with a PKR-specific antibody (provided by Dr. Mike Mathews, Cold Spring Harbor Laboratory), confirming that it was indeed PKR.

Example 7

PKR Inactivation or Deletion Results in Enhanced Infectibility of Untransformed Cells If PKR phosphorylation is responsible for the shut-off of viral gene translation in NIH-3T3 cells, and one of the functions of the activated oncogene product(s) in the transformed cells is the prevention of this phosphorylation event, then inhibition of PKR phosphorylation in NIH-3T3 cells by other means (e.g. drugs) should result in the enhancement of viral protein synthesis, and hence infection, in these cells. To test this idea, 2-aminopurine was used. This drug has been shown to possess relatively specific inhibitory activity towards PKR autophosphorylation (Samuel, C. E. and Brody, M., (1990) *Virology*, 176:106–113; Hu, Y. and Conway, T. W. (1993), *J. Interferon Res.*, 13:323–328). Accordingly, NIH 3T3 cells were exposed to 5 mM 2-aminopurine concurrently with exposure to reovirus. The cells were labeled with [$^{35}$S]methionine from 12 to 48 h postinfection, and lysates were harvested and analyzed by SDS-PAGE.

The results demonstrated that exposure to 2-aminopurine resulted in a significantly higher level of viral protein synthesis in NIH 3T3 cells (not shown). The enhancement was particularly pronounced after immunoprecipitating the lysates with an anti-reovirus serum. These results demonstrate that PKR phosphorylation leads to inhibition of viral gene translation, and that inhibition of this phosphorylation event releases the translation block. Therefore, intermediates in the Ras signalling pathway negatively regulate PKR, leading to enhanced infectibility of Ras-transformed cells.

Interferon β, known to induce PKR expression, was found to significantly reduce reovirus replication in Ras-transformed cells (data not shown).

A more direct approach to defining the role of PKR in reovirus infection is through the use of cells that are devoid of PKR. Accordingly, primary embryo fibroblasts from wild-type PKR $^{+/+}$ and PKR $^{0/0}$ mice (Yang, Y. L. et al. *EMBO J.* 14:6095–6106 (1995)) were compared in terms of susceptibility to reovirus infection. The results clearly showed that reovirus proteins were synthesized at a significantly higher level in the PKR $^{0/0}$ cells than in the PKR $^{+/+}$ cells. These experiments demonstrated that PKR inactivation or deletion enhanced host cell susceptibility to reovirus infection in the same way as does transformation by Ras or elements of the Ras signaling pathway, thereby providing strong support of the role of elements of the Ras signaling pathway in negatively regulating PKR.

Example 8

Inactivation of PKR in Transformed Cells Does Not Involve MEK

Receptor tyrosine kinases such as EGFRs are known to stimulate the mitogen-activated or extracellular signal-regulated kinases (ERK½) via Ras (see Robinson, M. J. and Cobb, M. H., *Curr. Opin. Cell. Biol.* 9:180–186 (1997)). This stimulation requires the phosphorylation of ERK½ by the mitogen-activated extracellular signal-regulated kinase, kinase MEK, which itself is activated (phosphorylated) by Raf, a serine-threonine kinase downstream of Ras. To determine if MEK activity was required for PKR inactivation in transformed cells, the effect of the recently identified MEK inhibitor PD98059 (Dudley, D. T. et al., *Proc. Natl. Acad. Sci. USA* 92:7686–7689 (1995); Waters, S. D. et al., *J Biol. Chem.* 270:20883–20886 (1995)) on infected Ras-transformed cells was studied.

H-Ras-transformed cells were grown to 80% confluency and infected with reovirus at an MOI of approximately 10 p.f.u./cell. PD98059 (Calbiochem), dissolved in dimethyl-sulfoxide (DMSO), was applied to the cells at the same time as the virus (final concentration of PD98059 was 50 μM). The control cells received an equivalent volume of DMSO. The cells were labeled with $^{35}$S-methionine from 12 to 48 hours post-infection. Lysates were then prepared, immunoprecipitated with the polyclonal anti-reovirus serotype 3 serum and analyzed by SDS-PAGE.

The results (data not shown) showed that PD98059, at a concentration that effectively inhibited ERK½ phosphorylation, did not inhibit reovirus protein synthesis in the transformed cells. On the contrary, PD98059 treatment consistently caused a slight enhancement of viral protein synthesis in these cells; the reason for this is under investigation. Consistent with the lack of inhibition of viral protein synthesis in the presence of PD98059, the PKR in these cells remained unphosphorylated (data not shown). As expected, PD98059 had no effect on reovirus-induced PKR phosphorylation in untransformed NIH-3T3 cells (data not shown). These results indicated that MEK and ERK½ are not involved in PKR activation.

Example 9

In Vivo Oncolytic Capability of Reovirus

A severe combined immunodeficiency (SCID) host tumor model was used to assess the efficacy of utilizing reovirus for tumor reduction. Male and female SCID mice (Charles River, Canada) were injected with v-erbB-transformed NIH 3T3 mouse fibroblasts (designated THC-11 cells) in two subcutaneous sites overlying the hind flanks. In a first trial, an injection bolus of $2.3 \times 10^5$ cells in 100 μl of sterile PBS was used. In a second trial, an injection bolus of $4.8 \times 10^6$ cells in 100 μl PBS was used. Palpable tumors were evident approximately two to three weeks post injection.

Reovirus serotype three (strain Dearing) was injected into the right-side tumor mass (the "treated tumor mass") in a volume of 20 μl at a concentration of $1.0 \times 10^7$ plaque forming units (PFU)/ml. The left-side tumor mass (the "untreated tumor mass") was left untreated. The mice were observed for a period of seven days following injection with reovirus, measurements of tumor size were taken every two days using calipers, and weight of tumors was measured after sacrifice of the animals. All mice were sacrificed on the seventh day. Results are shown in Table 1.

TABLE 1

Tumor Mass after Treatment with Reovirus

| Trial 1 (n = 8) | mean untreated tumor mass | 602 mg |
| | mean treated tumor mass | 284 mg |
| Trial 2 (n = 12) | mean control tumor mass | 1523.5 mg |
| | mean untreated tumor mass | 720.9 mg |
| | mean treated tumor mass | 228.0 mg |

The treated tumor mass was 47% of that of the untreated tumor mass in trial 1, and 31.6% of the untreated tumor mass in trial 2. These results indicated that the virus-treated tumors were substantially smaller than the untreated tumors, and that there may be an additional systemic effect of the virus on the untreated tumor mass.

Similar experiments were also conducted using unilateral introduction of tumor cells. SCID mice were injected subcutaneously and unilaterally in the hind flank with v-erbB-transformed NIH 3T3 mouse fibroblasts (THC-11 cells). Palpable tumors (mean area 0.31 cm²) were established after two weeks. Eight animals were then given a single intratumoral injection of $1.0 \times 10^7$ PFUs of reovirus serotype 3 (strain Dearing) in phosphate-buffered saline (PBD). Control tumors (n=10) were injected with equivalent amounts of UV-inactivated virus. Tumor growth was followed for 12 days, during which time no additional reovirus treatment was administered.

Figure 2:
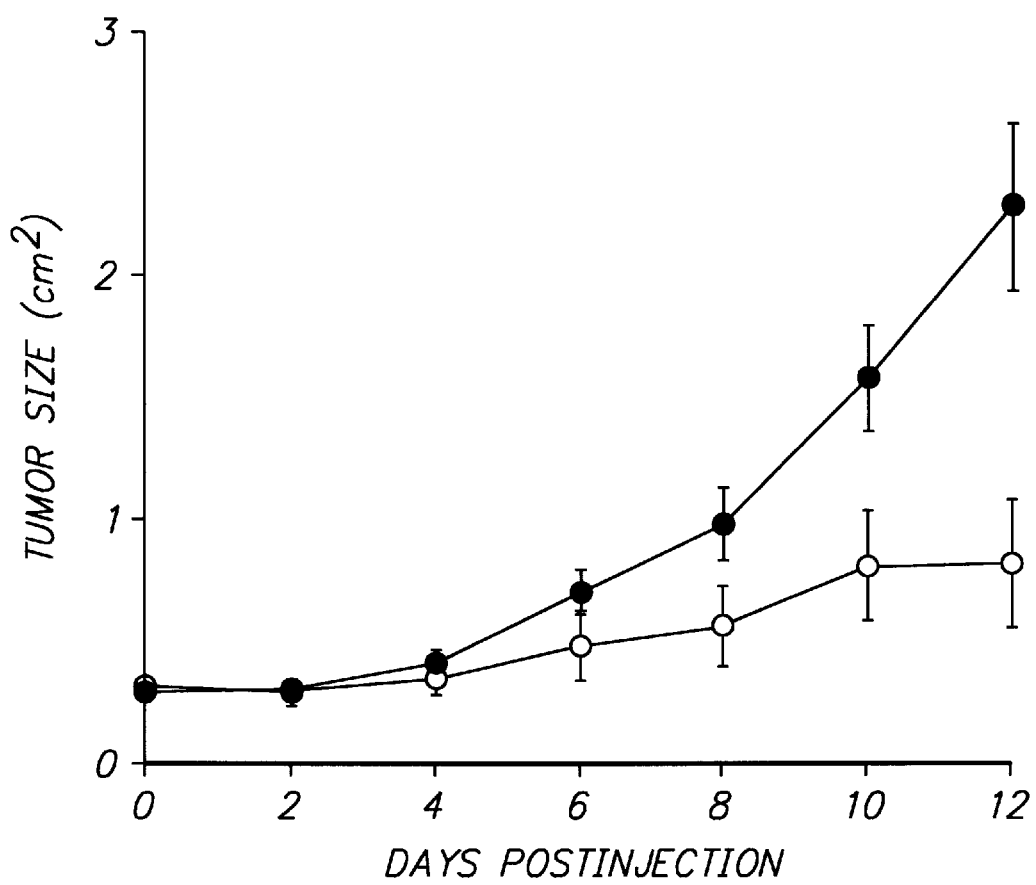
FIG. 2 is a graphic representation of the effects over time of active (open circles) or inactivated (closed circles) reovirus serotype 3 (strain Dearing) on the size of murine THC-11 tumors grown in severe combined immunodeficiency (SCID) mice. The plotted values represent the mean of the measurements with the standard error of the mean also shown.

Results, shown in FIG. 2, demonstrated that treatment of these tumors with a single dose of active reovirus (open circles) resulted in dramatic repression of tumor growth by the thirteenth day (endpoint), when tumors in the control animals injected with a single dose of inactivated reovirus (closed circles) exceeded the acceptable tumor burden. This experiment was repeated several times and found to be highly reproducible, thus further demonstrating the efficacy of reovirus in repressing tumor growth.

Example 10

In Vivo Oncolytic Capability of Reovirus Against Human Breast Cancer-Derived Cell Lines In vivo studies were also carried out using human breast carcinoma cells in a SCID mouse model. Female SCID mice were injected with $1 \times 10^6$ human breast carcinoma MDA-MB468 cells in two subcutaneous sites, overlying both hind flanks. Palpable tumors were evident approximately two to four weeks post injection. Undiluted reovirus serotype three (strain Dearing) was injected into the right side tumor mass in a volume of 20 μl at a concentration of $1.0 \times 10^7$ PFU/ml. The following results were obtained:

TABLE 2

Tumor Mass After Treatment with Reovirus

| TREATMENT | mean untreated tumor mass (left side) | mean treated tumor mass (right side) |
|---|---|---|
| Reovirus (N = 8) | 29.02 g | 38.33 g |
| Control (N = 8) | 171.8 g | 128.54 g |

*Note: One of the control mice died early during the treatment phase. None of the reovirus-treated mice died.

Although these studies were preliminary, it was clear that the size of the tumors in the reovirus-treated animals was substantially lower than that in the untreated animals. However, the size of the tumors on the right (treated) side of the reovirus-treated animals was slightly larger on average than the left (untreated) side. This was unexpected but may be explained by the composition of the mass being taken up by inflammatory cells with subsequent fibrosis, as well as by the fact that these tumors were originally larger on the right side on average than the left. The histologic composition of the tumor masses is being investigated. These results also support the systemic effect the reovirus has on the size of the untreated tumor on the contralateral slide of reovirus injection.

Example 11

Susceptibility of Additional Human Tumors to Reovirus Oncolysis

In view of the in vivo results presented above, the oncolytic capability observed in murine cells was investigated in cell lines derived from additional human tumors.
Cells and Virus All cell lines were grown in Dulbecco's modified Eagle's medium (DMEM) containing 10% fetal bovine serum (FBS).

The Dearing strain of reovirus serotype 3 used in these studies was propagated in suspension cultures of L cells and purified according to Smith (Smith, R. E. et al., (1969) *Virology*, 39:791–800) with the exception that β-mercaptoethanol (β-ME) was omitted from the extraction buffer. Reovirus labelled with [$^{35}$S]methionine was grown and purified as described by McRae and Joklik (McRae, M. A. and Joklik, W. K., (1978) *Virology*, 89:578–593). The particle/PFU ration for purified reovirus was typically 100/1.
Cytopathic Effects of Reovirus on Cells Confluent monolayers of cells were infected with reovirus serotype 3 (strain Dearing) at a multiplicity of infection (MOI) of approximately 40 plaque forming units (PFU) per cell. Pictures were taken at 36 hour postinfection for both reovirus-infected and mock-infected cells.

Immunofluorescent Analysis of Reovirus Infection

For the immunofluorescent studies the cells were grown on coverslips, and infected with reovirus at a multiplicity of infection (MOI) of ~10 PFU/cell or mock-infected as described above. At various times postinfection, cells were fixed in an ethanol/acetic acid (20/1) mixture for 5 minutes, then rehydrated by subsequential washes in 75%, 50% and 25% ethanol, followed by 4 washes with phosphate-buffered saline (PBS). The fixed and rehydrated cells were then exposed to the primary antibody (rabbit polyclonal anti-reovirus type 3 serum diluted 1/100 in PBS) for 2 hr at room temperature. Following 3 washes with PBS, the cells were exposed to the secondary antibody [goat anti-rabbit IgG (whole molecule) fluorescein isothiocyanate (FITC) conjugate diluted 1/100 in PBS containing 10% goat serum and 0.005% Evan's Blue counterstain] for 1 hour at room temperature. Finally, the fixed and treated cells were washed 3 more times with PBS, followed by 1 wash with double-distilled water, dried and mounted on slides in 90% glycerol containing 0.1% phenylenediamine, and viewed with a Zeiss Axiophot microscope mounted with a Carl Zeiss camera (magnification for all pictures was 200×).

Infection of Cells and Quantitation of Virus

Confluent monolayers of cells grown in 24-well plates were infected with reovirus at an estimated multiplicity of 10 PFU/cell. After 1 hour incubation at 37° C., the monolayers were washed with warm DMEM-10% FBS, and then incubated in the same medium. At various times postinfection, a mixture of NP-40 and sodium deoxycholate was added directly to the medium on the infected monolayers to final concentrations of 1% and 0.5%, respectively. The lysates were then harvested and virus yields were determined by plaque titration on L-929 cells.

Radiolabelling of Reovirus-Infected Cells and Preparation of Lysates

Confluent monolayers of cells were infected with reovirus (MOI~10 PFU/cell). At various times postinfection, the media was replaced with methionine-free DMEM containing 10% dialyzed PBS and 0.1 mCi/ml [$^{35}$S]methionine. After further incubation for 1 hour at 37° C., the cells were washed in phosphate-buffered saline (PBS) and lysed in the same buffer containing 1% Triton X-100, 0.5% sodium deoxycholate and 1 mM EDTA. The nuclei were then removed by low speed centrifugation and the supernatants was stored at 70° C. until use.

Immunoprecipitation and SDS-PAGE Analysis

Immunoprecipitation of [$^{35}$S]-labelled reovirus-infected cell lysates with anti-reovirus serotype 3 serum was carried out as previously described (Lee, P. W. K. et al. (1981) Virology, 108:134–146). Immunoprecipitates were analyzed by discontinuous SDS-PAGE according to the protocol of Laemmli (Laemmli, U.K., (1970) Nature, 227:680–685).

Breast Cancer

The c-erbB-2/neu gene encodes a transmembrane protein with extensive homology to the EGFR that is overexpressed in 20–30% of patients with breast cancer (Yu, D. et al. (1996) Oncogene 13:1359). Since it has been established herein that Ras activation, either through point mutations or through augmented signaling cascade elements upstream of Ras (including the c-erbB-2/neu homologue EGFR) ultimately creates a hospitable environment for reovirus replication, an array of cell lines derived from human breast cancers were assayed for reovirus susceptibility. The cell lines included MDA-MD-435SD (ATCC deposit HTB-129), MCF-7 (ATCC deposit HTB-22), T-27-D (ATCC deposit HTB-133), BT-20 (ATCC deposit HTB-19), HBL-100 (ATCC deposit HTB-124), MDA-MB-468 (ATCC deposit HTB-132), and SKBR-3 (ATCC deposit HTB-30).

Based upon induction of cytopathic effects, and viral protein synthesis as measured by radioactive metabolic labeling and immunofluorescence as described above, it was found that five out of seven of the tested breast cancers were susceptible to reovirus infection: MDA-MB-435S, MCF-7, T-27-D, MDA MB-468, and SKBR-3 were exquisitely sensitive to infection, while BT-20 and HBL-100 demonstrated no infectibility.

Brain Glioblastoma

Next a variety of cell lines derived from human brain glioblastomas was investigated. The cell lines included A-172, U-118, U-178, U-563, U-251, U-87 and U-373 (cells were a generous gift from Dr. Wee Yong, University of Calgary).

Six out of seven glioblastoma cell lines demonstrated susceptibility to reovirus infection, including U-118, U-178, U-563, U-251, U-87 and U-373, while A-172 did not demonstrate any infectibility, as measured by cytopathic effects, immunofluorescence and [$^{35}$S]-methionine labeling of reovirus proteins.

The U-87 glioblastoma cell line was investigated further. To assess the sensitivity of U-87 cells to reovirus, U-87 cells (obtained from Dr. Wee Yong, University of Calgary) were grown to 80% confluency and were then challenged with reovirus at a multiplicity of infection (MOI) of 10. Within a period of 48 hours there was a dramatic, widespread cytopathic effect (data not shown). To demonstrate further that the lysis of these cells was due to replication of reovirus, the cells were then pulse-labeled with [$^{35}$S]methionine for three hour periods at various times postinfection and proteins were analyzed by sodium dodecyl sulfate-polyacrylamide gel electrophoresis (SDS-PAGE) as described above. The results (not shown) clearly demonstrated effective reovirus replication within these cells with resultant shutoff of host protein synthesis by 24 hours postinfection.

Figure 3:
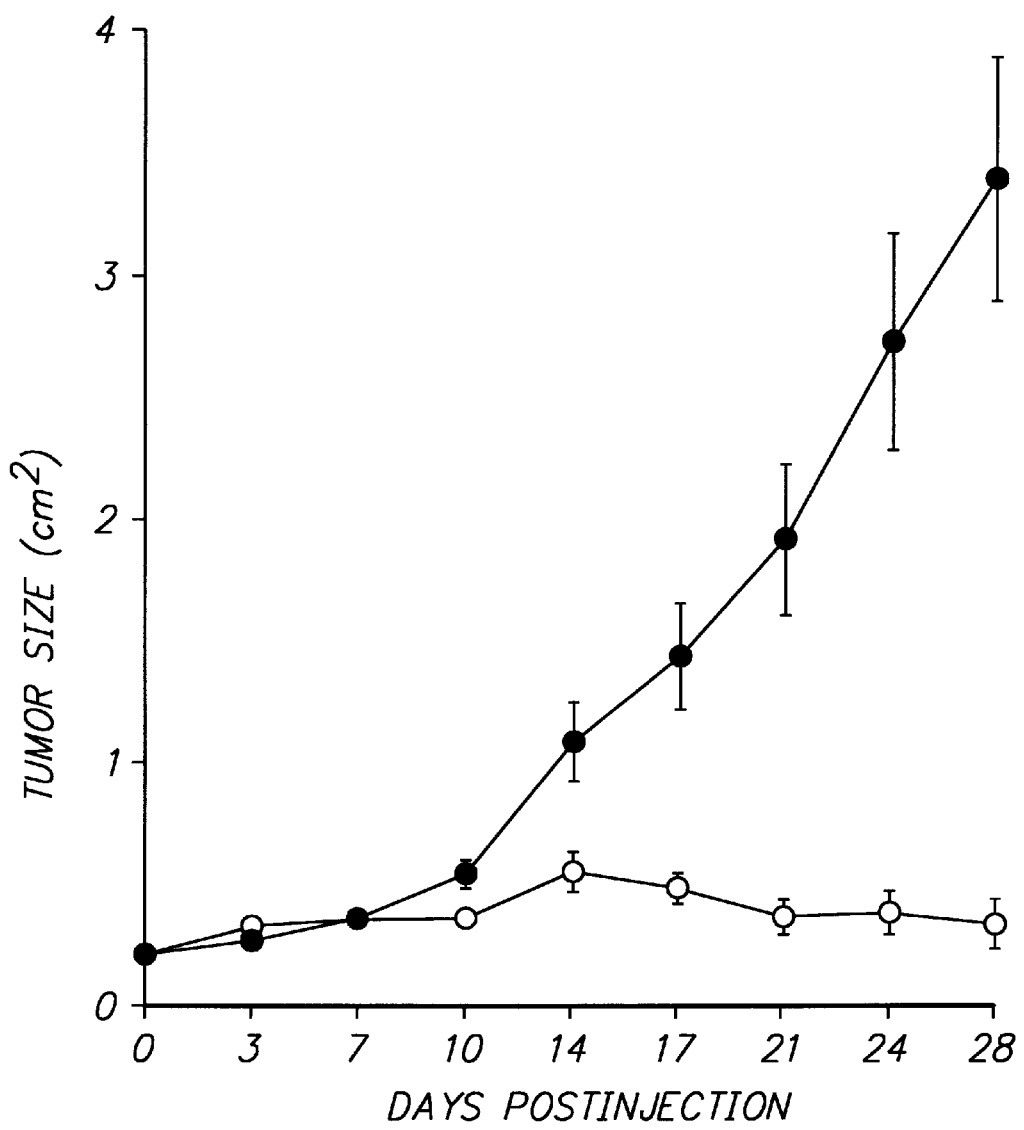
FIG. 3 is a graphic representation of the effects over time of active (open circles) or inactivated (closed circles) reovirus serotype 3 (strain Dearing) on the size of human glioblastoma U-87 xenografts grown in SCID mice. The plotted values represent the mean of the measurements with the standard error of the mean also shown.

The U-87 cells were also introduced as human tumor xenografts into the hind flank of 10 SCID mice. U-87 cells were grown in Dulbecco's modified Eagle's medium containing 10% fetal bovine serum, as described above. Cells were harvested, washed, and resuspended in sterile PBS; $2.0 \times 10^6$ cells in 100 µl were injected subcutaneously at a site overlying the hind flank in five- to eight-week old male SCID mice (Charles River, Canada). Tumor growth was measured twice weekly for a period of four weeks. Results, shown in FIG. 3, demonstrated that treatment of U-87 tumors with a single intratumoral injection of $1.0 \times 10^7$ PFUs of live reovirus (open circles, n=5) resulted in drastic repression of tumor growth, including tumor regression by the fourth week post-treatment (P=0.008), in comparison with treatment of tumors with a single intratumoral injection of the same amount of UV-inactivated reovirus (closed circles, n=5).

Hematoxylin/eosin (HE)-staining of the remaining microfoci of the tumors treated with active virus, performed as described (H. Lyon, Cell Biology, A Laboratory Handbook, J. E. Celis, ed., Academic Press, 1994, p. 232) revealed that the remaining tumor mass consisted largely of normal stroma without appreciable numbers of viable tumor cells, nor was there any evidence of infiltration of tumor cells into the underlying skeletal muscle (data not shown). Necrosis of tumor cells was due to direct lysis by the virus, the same mechanism of cell killing as by reovirus in vitro.

To determine if there was viral spread beyond the tumor mass, immunofluorescent microscopy using antibodies directed against total reovirus proteins was conducted as described above, on paraffin sections of the tumor and adjoining tissue. It was found that reovirus-specific proteins were confined to the tumor mass; no viral staining was detected in the underlying skeletal muscle (data not shown). As expected, viral proteins were not present in tumors injected with the UV-inactivated virus (data not shown). These results demonstrated that reovirus replication in these animals was highly tumor specific with viral amplification only in the target U-87 cells.

Since most tumors are highly vascularized, it was likely that some virus could enter the blood stream following the lysis of the infected tumor cells. To determine if there was systemic spread of the virus, blood was harvested from the treated and control animals, and serially diluted for subsequent plaque titration. Infectious virus was found to be present in the blood at a concentration of $1 \times 10^5$ PFUs/ml (data not shown).

The high degree of tumor specificity of the virus, combined with systemic spread, suggested that reovirus could be able to replicate in glioblastoma tumors remote from the initially infected tumor, as demonstrated above with regard to breast cancer cells. To verify this hypothesis, SCID mice were implanted bilaterally with U-87 human tumor xenografts on sites overlying each hind flank of the animals. These tumors were allowed to grow until they measured 0.5×0.5 cm. The left-side tumors were then injected with a single dose ($1 \times 10^7$ pfu) of reovirus in treated animals (n=5); control animals (n=7) were mock-treated with UV-inactivated virus. Tumors were again measured twice weekly for a period of four weeks.

Figure 4:
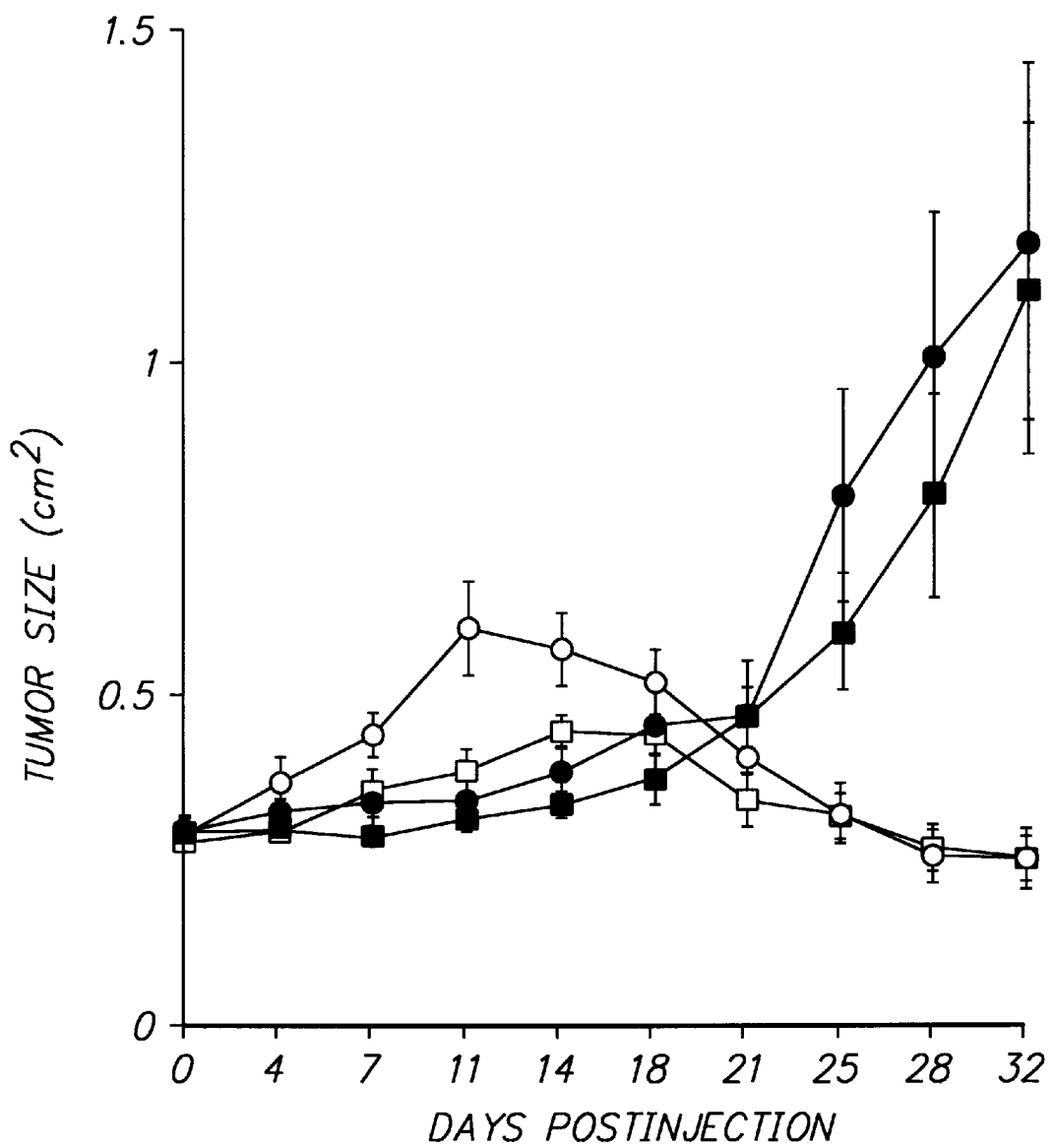
FIG. 4 is a graphic representation of the effects over time of active (open circles, open squares) or inactivated (closed circles, closed squares) reovirus serotype 3 (strain Dearing) on the size of injected/treated (open and closed circles) or untreated (open and closed squares) bilateral human glioblastoma U-87 xenografts grown in SCID mice. The plotted values represent the mean of the measurements with the standard error of the mean also shown.

Results, shown in FIG. 4, demonstrated that inhibition and eventual regression of both the treated/injected (circles) and untreated tumor masses (squares) occurred only in the live reovirus-treated animals (open circles and squares), in contrast with the inactivated reovirus-treated animals (closed circles and squares). Subsequent immunofluorescent analysis revealed that reovirus proteins were present in both the ipsilateral (treated) as well as the contralateral (untreated) tumor, indicating that regression on the untreated side was a result of reovirus oncolysis (data not shown).

Pancreatic Carcinoma

Cell lines derived from pancreatic cancer were investigated for their susceptibility to reovirus infection. The cell lines included Capan-1 (ATCC deposit HTB-79), BxPC3 (ATCC deposit CRL-1687), MIAPACA-2 (ATCC deposit CRL-1420), PANC-1 (ATCC deposit CRL-1469), AsPC-1 (ATCC deposit CRL-1682) and Hs766T (ATCC deposit HTB-134).

Five of these six cell lines demonstrated susceptibility to reovirus infection including Capan-1, MIAPACA-2, PANC-1, AsPC-1 and Hs766T, whereas BxPC3 demonstrated little infectability as assayed by virus-induced cytopathological effects, immunofluorescence and [$^{35}$S]-labelling. Interestingly, four of the five cell lines demonstrating susceptibility to reovirus oncolysis have been shown to possess transforming mutations in codon 12 of the K-ras gene (Capan-1, MIAPACA-2, PANC-1 and AsPC-1) whereas the one lacking such susceptibility (BxPC3) has been shown to lack such a mutation (Berrozpe, G., et al. (1994), *Int. J. Cancer*, 58:185–191). The status of the other K-ras codons is currently unknown for the Hs766T cell line.

Example 12

Use of Reovirus as an Oncolytic Agent in Immune-Competent Animals

A syngeneic mouse model was developed to investigate use of reovirus in immune-competent animals rather than in SCID mice as described above. C3H mice (Charles River) were implanted subcutaneously with $1.0 \times 10^6$ PFUs ras-transformed C3H cells (a gift of D. Edwards, University of Calgary). Following tumor establishment, mice were treated with a series of intratumoral injections of either live reovirus ($1.0 \times 10^8$ PFUs) or UV-inactivated reovirus. Following an initial series (six injections over a nine-day course), test animals received a treatment of dilute reovirus ($1.0 \times 10^7$ PFUs) every second day. Mock-treated animals received an equivalent amount of UV-inactivated virus.

Figure 5:
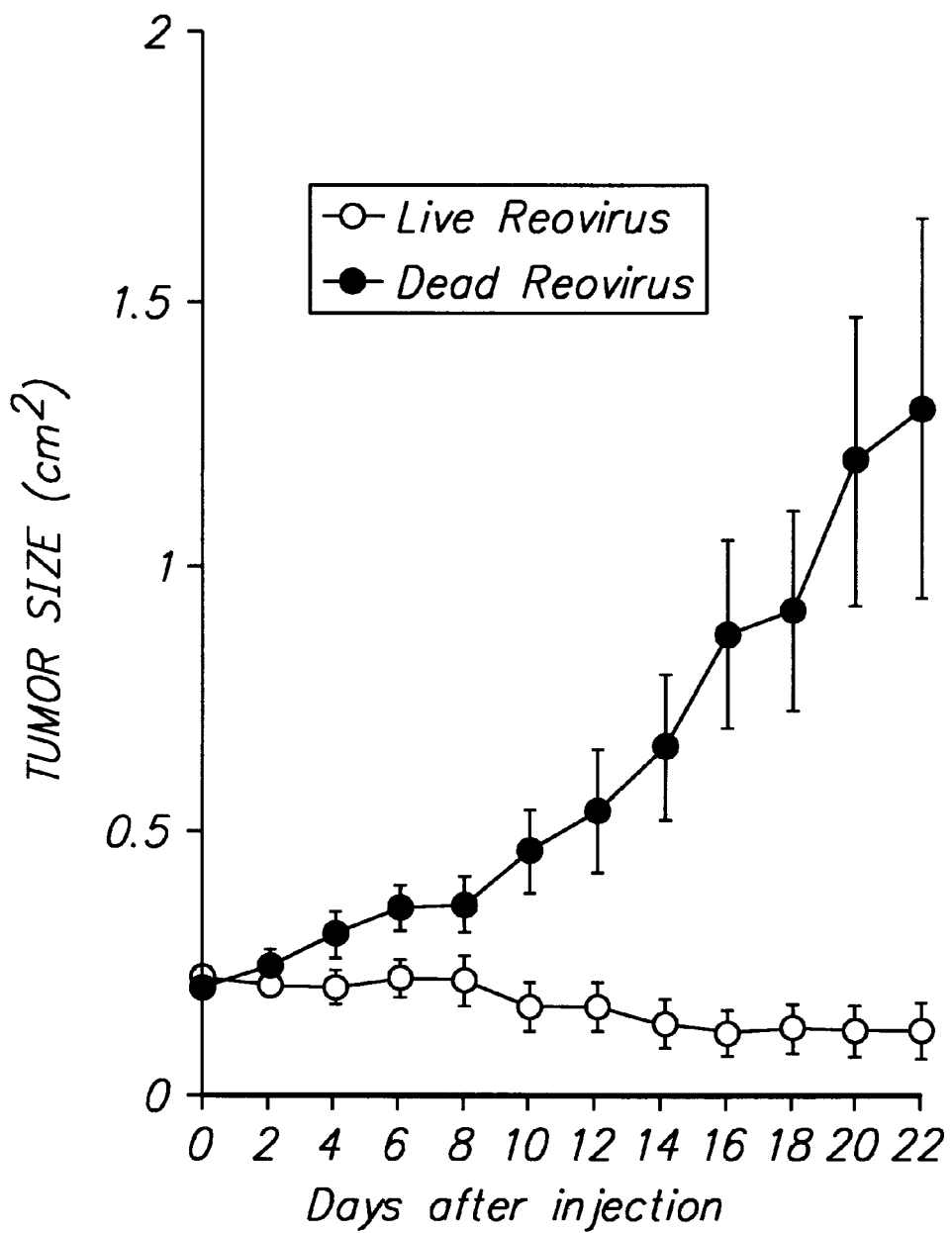
FIG. 5 is a graphic representation of the effects over time of active (open circles) or inactivated (closed circles) reovirus serotype 3 (strain Dearing) on the size of C3H transformed cell mouse tumors in immunocompetent C3H mice.

FIG. 5 demonstrates that reovirus was an effective oncolytic agent in these immune competent animals. All of the test animals showed regression of tumors; 5 of the 9 test animals exhibited complete tumor regression after 22 days, a point at which the control animals exceeded acceptable tumor burden. Furthermore, there were no identifiable side effects in the animals treated with reovirus.

To assess the effects of previous reovirus exposure on tumor repression and regression, one-half of a test group was challenged with reovirus (intramuscular injection of $1.0 \times 10^8$ PFUs, type 3 Dearing) prior to tumor establishment. Two weeks after challenge, neutralizing antibodies could be detected in all exposed animals. Following tumor establishment, animals were treated with a series of intratumoral injections of either live or UV-inactivated reovirus, as described above.

Figure 6:
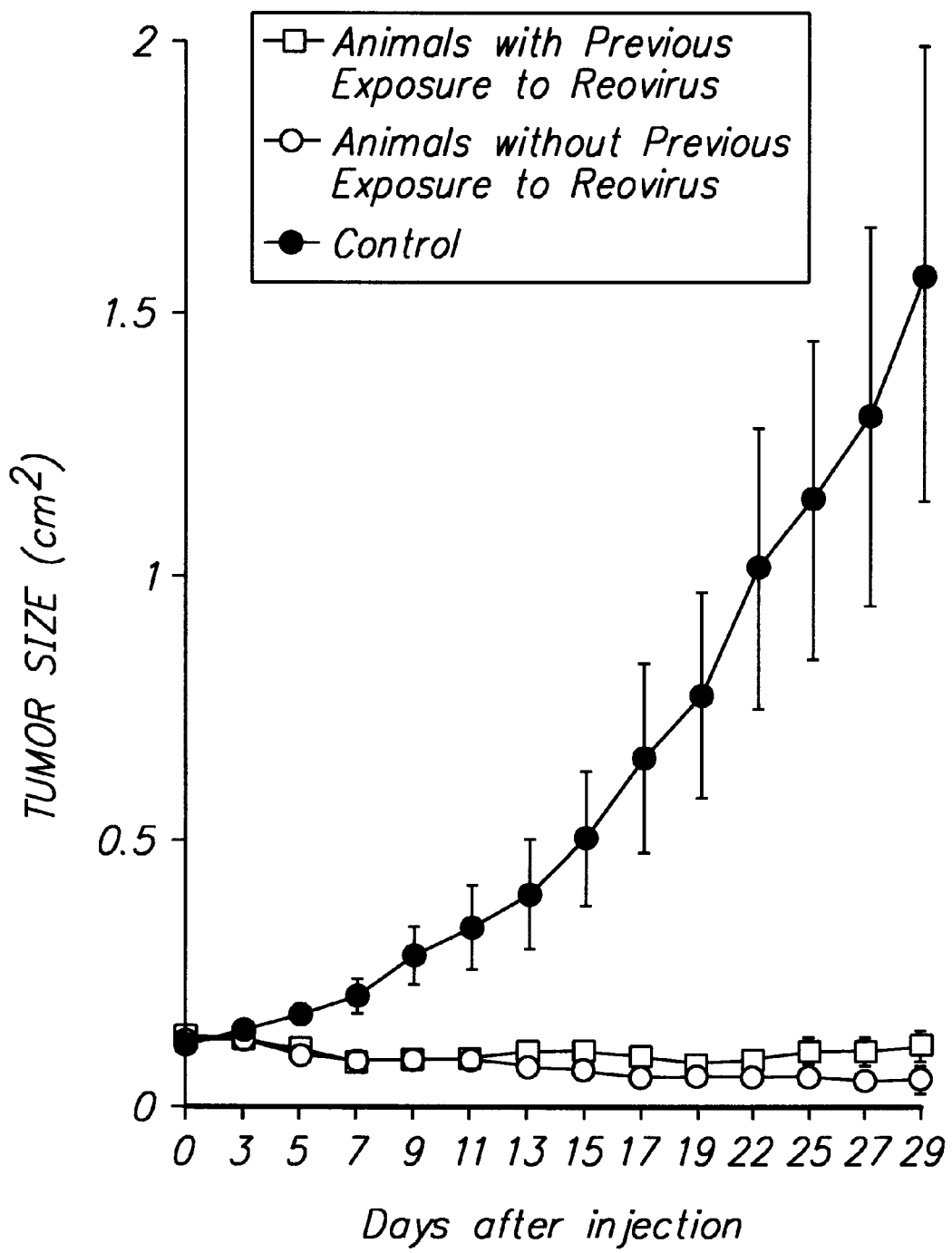
FIG. 6 is a graphic representation of the effects over time of active (open circles, open squares) or inactivated (closed circles) reovirus serotype 3 (strain Dearing) on the size of C3H transformed cell mouse tumors grown in immunocompetent C3H mice previously exposed (open squares) or unexposed (open circles) to reovirus.

FIG. 6 demonstrates that animals with circulating neutralizing antibodies to reovirus (i.e., those challenged with reovirus prior to tumor establishment) exhibited tumor repression and regression similar to those animals in which there was no prior exposure to reovirus. Thus, reovirus can serve as an effective oncolytic agent even in immune-competent animals with previous exposure to reovirus.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating a ras-mediated proliferative disorder in a mammal suffering from said disorder, wherein said mammal is selected from the group consisting of dogs, cats, sheep, goats, cattle, horses, pigs, humans and non-human primates, and wherein said method comprises administering to said mammal an effective amount of at least one reovirus in the absence of BCNU under conditions which result in substantial lysis of the ras-mediated proliferating cells in said mammal.

2. The method of claim 1, wherein the reovirus is selected from the group consisting of a mammalian reovirus and an avian reovirus.

3. The method of claim 2, wherein the reovirus is a mammalian reovirus.

4. The method of claim 3, wherein the reovirus is a human reovirus.

5. The method of claim 4, wherein the reovirus is selected from the group consisting of serotype 1 reovirus, serotype 2 reovirus and serotype 3 reovirus.

6. The method of claim 5, wherein the reovirus is a serotype 3 reovirus.

7. The method of claim 2, wherein the reovirus is an avian reovirus.

8. The method of claim 1, wherein more than one type of reovirus is administered.

9. The method of claim 1, wherein more than one strain of reovirus is administered.

10. The method of claim 1, wherein the reovirus is a field isolate.

11. The method of claim 1, wherein the ras-mediated proliferative disorder is a neoplasm.

12. The method of claim 1, wherein the ras-mediated proliferative disorder is neurofibromatosis.

13. The method of claim 11, wherein the neoplasm is a solid neoplasm.

14. The method of claim 11, wherein the neoplasm is selected from the group consisting of lung cancer, prostate cancer, colorectal cancer, thyroid cancer, renal cancer, adrenal cancer, liver cancer, pancreatic cancer, breast cancer and central and peripheral nervous system cancer.

15. The method of claim 14, wherein the neoplasm is a central nervous system cancer.

16. The method of claim 14, wherein the neoplasm is a breast cancer.

17. The method of claim 11, wherein the neoplasm is a hematopoietic neoplasm.

18. The method of claim 13, wherein the reovirus is administered by injection into or near the solid neoplasm.

19. The method of claim 1, wherein the reovirus is administered intravenously into the mammal.

20. The method of claim 1, wherein the reovirus is administered intraperitoneally into the mammal.

21. The method of claim 1 wherein the mammal is immunocompetent.

22. The method of claim 1, wherein the mammal is a human.

23. The method of claim 1, wherein approximately 1 to $10^{15}$ plaque forming units of reovirus/kg body weight are administered.

24. The method of claim 1, wherein the reovirus is administered in a single dose.

25. The method of claim 1, wherein the reovirus is administered in more than one dose.

26. The method of claim 11, wherein the neoplasm is metastatic.

27. The method of claim 1 further comprising the administration of an effective amount of a chemotherapeutic agent, with the proviso that the chemotherapeutic agent is not BCNU.

28. A method of treating a ras-mediated proliferative disorder in a mammal wherein said mammal is selected from the group consisting of dogs, cats, sheep, goats, cattle, horses, pigs, humans and non-human primates, and wherein said method comprises administering to the ras-mediated proliferating cells of the mammal an effective amount of at least one modified reovirus under conditions which result in substantial lysis of the ras-mediated proliferating cells.

29. The method of claim 11, wherein the reovirus is treated with a protease prior to administration.

30. A method of treating a ras-mediated neoplasm in a human, comprising administering to the neoplasm an effective amount of reovirus to result in substantial oncolysis of the cells of the neoplasm.

31. The method of claim 30, wherein the neoplasm is a solid neoplasm and the reovirus is administered by injection into or near the neoplasm.

32. The method of claim 31, wherein the solid neoplasm is a pancreatic cancer.

33. A method of inhibiting ras-mediated metastases of a neoplasm in a mammal wherein said mammal is selected from the group consisting of dogs, cats, sheep, goats, cattle, horses, pigs, humans and non-human primates, and wherein said method comprises administering to the neoplastic cells of said mammal a reovirus in an amount sufficient to result in substantial lysis of the neoplastic cells.

34. A method of treating a suspected ras-mediated neoplasm in a mammal, comprising surgical removal of substantially all of the neoplasm and administration of a reovirus to the site of the surgical removal in an amount sufficient to result in substantial oncolysis of any remaining neoplastic cells.

35. A pharmaceutical composition comprising a reovirus, a chemotherapeutic agent and a pharmaceutically acceptable excipient with the proviso that the chemotherapeutic agent is not BCNU.

36. A kit comprising a pharmaceutical composition comprising a reovirus and a chemotherapeutic agent with the proviso that the chemotherapeutic agent is not BCNU.

* * * * *

UNITED STATES PATENT AND TRADEMARK OFFICE
CERTIFICATE OF CORRECTION

PATENT NO.   : 6,136,307                                                Page 1 of 1
DATED        : October 24, 2000
INVENTOR(S)  : Patrick W. Lee, James Strong and Matthew C. Coffey It is certified that error appears in the above-identified patent and that said Letters Patent is hereby corrected as shown below:

<u>Drawings,</u>
Figure 1, below the caption reading blocks translation initiation of viral genes, "PKA" should read -- PKR --.

Signed and Sealed this

Twenty-third Day of July, 2002

Attest:

Attesting Officer

JAMES E. ROGAN
Director of the United States Patent and Trademark Office